US008841511B2

(12) United States Patent
Maliga et al.

(10) Patent No.: US 8,841,511 B2
(45) Date of Patent: Sep. 23, 2014

(54) REMOVAL OF PLASTID SEQUENCES BY TRANSIENTLY EXPRESSED SITE-SPECIFIC RECOMBINASES

(75) Inventors: Pal Maliga, East Brunswick, NJ (US); Kerry A. Lutz, Somerset, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 2007 days.

(21) Appl. No.: 10/547,561

(22) PCT Filed: Mar. 3, 2004

(86) PCT No.: PCT/US2004/006492
§ 371 (c)(1),
(2), (4) Date: Jun. 21, 2006

(87) PCT Pub. No.: WO2004/078935
PCT Pub. Date: Sep. 16, 2004

(65) Prior Publication Data
US 2006/0260000 A1    Nov. 16, 2006

Related U.S. Application Data

(60) Provisional application No. 60/451,779, filed on Mar. 3, 2003, provisional application No. 60/535,069, filed on Jan. 8, 2004.

(51) Int. Cl.
C12N 15/82    (2006.01)

(52) U.S. Cl.
CPC ........ *C12N 15/8209* (2013.01); *C12N 15/8214* (2013.01); *C12N 15/8213* (2013.01)
USPC ...................................................... 800/278

(58) Field of Classification Search
CPC ...................... C12N 15/8213; C12N 15/8214
See application file for complete search history.

(56) References Cited

U.S. PATENT DOCUMENTS

| | | | |
|---|---|---|---|
| 5,571,694 A | 11/1996 | Makoff et al. | |
| 5,614,395 A | 3/1997 | Ryals et al. | |
| 5,686,079 A | 11/1997 | Curtiss, III et al. | |
| 5,877,402 A | 3/1999 | Maliga et al. | |
| 6,110,736 A | 8/2000 | Hodges et al. | |
| 6,149,919 A | 11/2000 | Domenighini et al. | |
| 6,297,054 B1 | 10/2001 | Maliga et al. | |
| 6,376,744 B1 | 4/2002 | Maliga et al. | |
| 6,388,168 B1 | 5/2002 | Maiga et al. | |
| 6,472,586 B1 | 10/2002 | Maliga et al. | |
| 6,723,896 B1 * | 4/2004 | Moller et al. | 800/288 |

FOREIGN PATENT DOCUMENTS

| | | |
|---|---|---|
| EP | 0 430 645 A2 | 6/1991 |
| WO | WO 01/21768 A2 | 3/2001 |
| WO | WO 01/29241 A1 | 4/2001 |
| WO | WO 01/77353 A2 | 10/2001 |
| WO | WO 02/079409 | 10/2002 |
| WO | WO 03/083086 | 10/2003 |

OTHER PUBLICATIONS

Gleave et al (1999, Plant Mol. Biol. 40:223-235).*
Kuroda et al (2001, Plant Physiol. 125:430-436).*
Lutz et al (2001, Plant Physiol. 125: 1585-1590).*
Corneille, S. Efficient elimination of selectable marker genes from the plastid genome by the CRE-lox site-specific recombination . . . The Plant Journal, 27(2): 171-178 (2001).
Hajdukiewicz, P. "Multiple pathways for Cre/lox-mediated recombination in plastids" The Plant Journal, 27(2): 161-170 (2001).
Daniell, H. "Marker free transgenic plants: engineering the chloroplast gene without the use of antibiotic selection" Curr. Genet., 39: 109-116 (2001).
Tacket, C. "Immunogenicity in humans of a recombinant bacterial antigen delivered in a transgenic potato" Nature Medicine, 4(5): 607-609 (1998).
Tacket, C. "A review of oral vaccination with transgenic vegetables" Microbes and Infection, 777-783 (1999).
Tregoning, J. "Expression of tetanus toxin Fragment C in tobacco chloroplasts" Nucleic Acids Research, 31(4): 1174-1179 (2003).
Bock, R. "Transgenic Plastids in Basic Research and Plant Biotechnology" J. Mol. Biol., 312: 425-438 (2001).
Magagnoli, C. "Mutations in the A Subunit Affect Yield, Stability, and Protease Sensitivity of Nontoxic Derivatives . . . " Infection and Immunity, 64(12): 5434-5438 (1996).
Iamtham, S., et al., "Removal of antibiotic resistance genes from transgenic tobacco plastids", Nature Biotechnology, 18:1172-1176, (Nov. 2000).
Khan, M.S. "Fluorescent antibiotic resistance marker for tracking plastid transformation in higher plants"; Nature Biotechnology, 17: 910-915 (1999).
Dale, E.C. "Gene transfer with subsequent removal of the selection gene from the host genome"; Proc. Natl. Acad. Sci. USA, 88: 10558-10562 (1991).
Srivastava, V. "Single-copy transgenic wheat generated through the resolution of complex integration patterns"; Proc. Natl. Acad. Sci. USA, 96: 11117-11121 (1999).
Le, Y. "Nuclear targeting determinants of the phage P1 Cre DNA recombinase"; Nucleic Acids Research, 27(24): 4703-4709 (1999).
Lyznik, L.A. "Activity of yeast FLP recombinase in maize and rice protoplasts"; Nucleic Acids Research, 21(4): 969-975 (1993).
Lyznik, L.A. "FLP-mediated recombination of FRT sites in the maize genome"; Nucleic Acids Research, 24(19): 3784-3789 (1996).
Zoubenko, O.V. "Efficient targeting of foreign genes into the tobacco plastid genome"; Nucleic Acids Research, 22(19): 3819-3824 (1994).
Love, J. "Stringent control of transgene expression in *Arabidopsis thaliana* using the Top10 promoter system"; The Plant Journal, 21(6): 579-588 (2000).
Serino, G. "A negative selection scheme based on the expression of cytosine deaminase in plastids"; The Plant Journal, 12(3): 697-701 (1997).

(Continued)

*Primary Examiner* — Anne Kubelik
(74) *Attorney, Agent, or Firm* — Dann, Dorfman, Herrell & Skillman; Kathleen D. Rigaut; Robert C. Netter, Jr.

(57) ABSTRACT

Compositions and methods for manipulating the plastid genome of higher plants are provided.

9 Claims, 10 Drawing Sheets

(56) References Cited

OTHER PUBLICATIONS

Lyznik, L.A. "Heat-inducible expression of FLP gene in maize cells"; The Plant Journal, 8(2): 177-186 (1995).
Soll, J. "Protein translocation into and across the chloroplastic envelope membranes"; Plant Molecular Biology, 38: 191-207 (1998).
Adams, D. "Cre-lox Recombination in *Escherichia coli* Cells Mechanistic Differences from the in Vitro Reaction"; J. Mol. Biol., 226: 661-673 (1992).
Craig, N.L. "The Mechanism of Conservative Site-Specific Recombination"; Annu. Rev. Genet., 22: 77-105 (1988).
Lichtenstein, C. "Prospects for reverse genetics in plants using recombination"; Plant Molecular Biology, 21: v-xii (1993).
Lubben, T.H. "Chloroplast import characteristics of chimeric proteins"; Plant Molecular Biology; 12: 13-18 (1989).
Russell, S.H. "Directed excision of a transgene from the plant genome"; Mol Gen Genet, 234: 49-59 (1992).
Timko, M.P. "Structure and Expression of Nuclear Genes Encoding Polypeptides of the Photosynthetic Apparatus"; Mol Biol of the Photosynthetic Apparatus, 381-396 (1985).
Timmermans, M.C.P. "The pFF plasmids: cassettes utilising CaMV sequences for expression of foreign genes in plants"; Journal of Biotechnology, 14: 333-344 (1990).
Wasmann, C.C. "The importance of the transit peptide and the transported protein for protein import into chloroplasts"; Mol Gen Genet, 205: 446-453 (1986).
Hajduikiewicz et al. "Multiple pathways for Cre/lox-mediated recombination in plastids"; Plant Journal, 27(2):161-170 (2001).
Corneille et al., "Efficient elimination of selectable marker genes from the plastid genome by the CRE-lox site-specific recombination . . . "; Plant Journal, 27(2):171-178 (2001).
Maliga, "Engineering th eplastid genome of higher plants"; Current Opinion in Plant Biology, 5(2):164-172 (2002).
Iamtham et al., "Removal of antibiotic resistance genes from transgenic tobacco plastids", Nature Biotechnology, 18(11):1172-1176 (2000).
Svab Z. et al., "High-frequency plastid transformation in tobacco by selection for a chimeric aadA gene", Proc Natl Acad Sci U S A, 90(3):913-917 (1993).
Haq T.A. et al., "Oral immunization with a recombinant bacterial antigen produced in transgenic plants", Science. May 5, 1995;268(5211):714-6.
Gianelli V. et al., "Protease susceptibility and toxicity of heat-labile enterotoxins with a mutation in the active site or in the . . . "Infect. Immun. 1997 65: 331-334.
Pizza M. et al., "A Genetically Detoxified Derivative of Heat-labile *Escherichia coli* Enterotoxin Induces Neutralizing . . . ": J. Exp. Med., 180:2147-2153 (1994).
Ma S.W. et al., "transgenic Plants expressing autoantigens fed to mice to induce oral immune tolerance", Nature Medicine 3(7):793-796 (1997).
Kuroda H. "complementarity of the 16s rRNA penultimate stem with sequences downstream of the AUG destabilizes th eplastid mRNAs", Nucleic Acids Research, 29(4):970-975 (2001).
Kuroda H. "Sequences Downstream of the Translation Initiation Codon are Important Determinants of Translatio Efficiency in Chloroplasts", Plant Phys,.125:430-436 (2001).
Ye G. "Plastid-expressed 5-enolpyruvylshikimate-3-phosphate synthase genes provide high level glyphosate tolerance in tobacco", The Plant Journal, 25(3):261-270 (2001).
Staub J.M. "High-yield production of human therapeutic protein in tobacco chloropasts", Nature Biotechnology, 18:333-338 (2000).
Heifetz P.B. "Genetic engineering of the chloroplast", Biochimie, 82:655-666 (2000).
Giddings G. "Transgenic plants as factories for biopharmaceiticals", Nature Biotechnology 18:1151-1155 (2000).
Douce G. "Genetically Detoxified Mutants of Heat-Labile Toxin from *Escherichia coli* Are Able to Act as Oral Adjuvants", Infection and Immunity, 67(9):4400-4406 (1999).
Douce G. "Mucosal immunogenicity of genetically detoxified derivatives of heat labile toxin from *Escherichia coli*", Vaccine 16(11/12): 1065-1073 (1998).
Barchfeld G.L. "The adjuvants MF59 and LT-K63 enhance th emucosal and systemic immunogenicity of subunit influenza vaccine administered in mice", Vaccien, 17:695-704 (1999).
Carrer H. "Kanamycin resistance as a selectable marker for plastid transformation in tobacco", Mol Gen Genet, 241:49-56 (1993).

* cited by examiner

SEQUENCE LISTING

<160> NUMBER OF SEQ ID NOS: 18

<210> SEQ ID NO 1
<211> LENGTH: 1162
<212> TYPE: DNA
<213> ORGANISM: Artificial Sequence

```
<220> FEATURE:
<223> OTHER INFORMATION: Synthetic Sequence

<400> SEQUENCE: 1
gaattcgagc tcggtacccg gggatccggt acatctagat gtaccataac ttcgtataat      60
gtatgctata cgaagttata gatcaattca gttgtaggga gggatttatg ggggaagcgg     120
tgatcgccga agtatcgact caactatcag aggtagttgg cgtcatcgag cgccatctcg     180
aaccgacgtt gctggccgta catttgtacg gctccgcagt ggatggcggc ctgaagccac     240
acagtgatat tgatttgctg gttacggtga ccgtaaggct tgatgaaaca cgcggcgag      300
ctttgatcaa cgacctttg gaaacttcgg cttccctgg agagagcgag attctccgcg       360
ctgtagaagt caccattgtt gtgcacgacg acatcattcc gtggcgttat ccagctaagc     420
gcgaactgca atttggagaa tggcagcgca atgacattct tgcaggtatc ttcgagccag     480
ccacgatcga cattgatctg gctatcttgc tgacaaaagc aagagaacat agcgttgcct     540
tggtaggtcc agcggcggag gaactctttg atccggttcc tgaacaggat ctatttgagg     600
cgctaaatga aaccttaacg ctatggaact cgccgcccga ctgggctggc gatgagcgaa     660
atgtagtgct tacgttgtcc cgcatttggt acagcgcagt aaccggcaaa atcgcgccga     720
aggatgtcgc tgccgactgg gcaatggagc gcctgccggc ccagtatcag cccgtcatac     780
ttgaagctag acaggcttat cttggacaag aagaagatcg cttggcctcg cgcgcagatc     840
agttggaaga atttgtccac tacgtgaaag gcgagatcac caaggtagtc ggcaaataat     900
gtctagctag ataacttcgt ataatgtatg ctatacgaag ttatagacat tagcagataa     960
attagcagga ataaagaag gataaggaga aagaactcaa gtaattatcc ttcgttctct     1020
taattgaatt gcaattaaac tcggcccaat cttttactaa aaggattgag ccgaatacaa    1080
caaagattct attgcatata ttttgactaa gtatatactt acctagatat acaagatttg    1140
aaatacaaaa tctagcaagc tt                                             1162

<210> SEQ ID NO 2
<211> LENGTH: 1911
<212> TYPE: DNA
<213> ORGANISM: Artificial Sequence
<220> FEATURE:
<223> OTHER INFORMATION: Synthetic Sequence

<400> SEQUENCE: 2
gaattcgagc tcgctccccc gccgtcgttc aatgagaatg gataagaggc tcgtgggatt      60
gacgtgaggg ggcagggatg gctatatttc tgggagaatt aaccgatcga cgtgcaagcg     120
gacatttatt ttaaattcga taattttgc aaaaacattt cgacatattt atttattta      180
ttattatgag aatcaatcct actacttctg gttctggggt ttccacggct agcccagaaa     240
gaagaccggc cgacatccgc cgtgccaccg aggcggacat gccggcggtc tgcaccatcg     300
tcaaccacta catcgagaca agcacggtca acttccgtac cgagccgcag gaaccgcagg     360
agtggacgga cgacctcgtc cgtctgcggg agcgctatcc ctggctcgtc gccgaggtgg     420
acggcgaggt cgccggcatc gcctacgcgg gcccctggaa ggcacgcaac gcctacgact     480
ggacggccga gtcgaccgtg tacgtctccc cgccgccacca gcggacggga ctgggctcca     540
cgctctacac ccacctgctg aagtccctgg aggcacaggg cttcaagagc gtggtcgctg     600
tcatcgggct gcccaacgac ccgagcgtgc gcatgcacga ggcgctcgga tatgcccccc     660
gcggcatgct gcgggcggcc ggcttcaagc acgggaactg gcatgacgtg ggtttctggc     720
```

-continued

| | |
|---|---|
| agctggactt cagcctgccg gtaccgcccc gtccggtcct gcccgtcacc gagatctgat | 780 |
| gatctagatg taccataact tcgtataatg tatgctatac gaagttatag atcaattcag | 840 |
| ttgtagggag ggatttatgg gggaagcggt gatcgccgaa gtatcgactc aactatcaga | 900 |
| ggtagttggc gtcatcgagc gccatctcga accgacgttg ctggccgtac atttgtacgg | 960 |
| ctccgcagtg gatggcggcc tgaagccaca cagtgatatt gatttgctgg ttacggtgac | 1020 |
| cgtaaggctt gatgaaacaa cgcggcgagc tttgatcaac gaccttttgg aaacttcggc | 1080 |
| ttcccctgga gagagcgaga ttctccgcgc tgtagaagtc accattgttg tgcacgacga | 1140 |
| catcattccg tggcgttatc cagctaagcg cgaactgcaa tttggagaat ggcagcgcaa | 1200 |
| tgacattctt gcaggtatct tcgagccagc cacgatcgac attgatctgg ctatcttgct | 1260 |
| gacaaaagca agagaacata gcgttgcctt ggtaggtcca gcggcggagg aactctttga | 1320 |
| tccggttcct gaacaggatc tatttgaggc gctaaatgaa accttaacgc tatggaactc | 1380 |
| gccgcccgac tgggctggcg atgagcgaaa tgtagtgctt acgttgtccc gcatttggta | 1440 |
| cagcgcagta accggcaaaa tcgcgccgaa ggatgtcgct gccgactggg caatggagcg | 1500 |
| cctgccggcc cagtatcagc ccgtcatact tgaagctaga caggcttatc ttggacaaga | 1560 |
| agaagatcgc ttggcctcgc gcgcagatca gttggaagaa tttgtccact acgtgaaagg | 1620 |
| cgagatcacc aaggtagtcg gcaaataatg tctagctaga taacttcgta taatgtatgc | 1680 |
| tatacgaagt tatagacatt agcagataaa ttagcaggaa ataaagaagg ataaggagaa | 1740 |
| agaactcaag taattatcct tcgttctctt aattgaattg caattaaact cggcccaatc | 1800 |
| ttttactaaa aggattgagc cgaatacaac aaagattcta ttgcatatat tttgactaag | 1860 |
| tatatactta cctagatata caagatttga aatacaaaat ctagcaagct t | 1911 |

<210> SEQ ID NO 3
<211> LENGTH: 1920
<212> TYPE: DNA
<213> ORGANISM: Artificial Sequence
<220> FEATURE:
<223> OTHER INFORMATION: Synthetic Sequence

<400> SEQUENCE: 3

| | |
|---|---|
| gaattcgagc tcggtaccca agctcccccc gccgtcgttc aatgagaatg gataagaggc | 60 |
| tcgtgggatt gacgtgaggg ggcagggatg gctatatttc tgggagcgaa ctccgggcga | 120 |
| atacgaagcg cttggataca gttgtaggga gggatccatg gctttgggat caatatcagc | 180 |
| aatgcagttc atccaacgat aaacttaatc cgaattatag agctacgaca caatcagcta | 240 |
| gcccagaaag aagaccggcc gacatccgcc gtgccaccga ggcggacatg ccggcggtct | 300 |
| gcaccatcgt caaccactac atcgagacaa gcacggtcaa cttccgtacc gagccgcagg | 360 |
| aaccgcagga gtggacggac gacctcgtcc gtctgcggga gcgctatccc tggctcgtcg | 420 |
| ccgaggtgga cggcgaggtc gccggcatcg cctacgcggg ccctggaag gcacgcaacg | 480 |
| cctacgactg gacggccgag tcgaccgtgt acgtctcccc cgccaccag cggacgggac | 540 |
| tgggctccac gctctacacc cacctgctga gtccctgga ggcacagggc ttcaagagcg | 600 |
| tggtcgctgt catcggctg cccaacgacc cgagcgtgcg catgcacgag cgctcggat | 660 |
| atgccccccg cggcatgctg cgggcggccg gcttcaagca cgggaactgg catgacgtgg | 720 |
| gtttctggca gctggacttc agcctgccgg taccgcccg tccggtcctg cccgtcaccg | 780 |
| agatctgatg atctagatgt accataactt cgtataatgt atgctatacg aagttataga | 840 |
| tcaattcagt tgtagggagg gatttatggg ggaagcggtg atcgccgaag tatcgactca | 900 |

-continued

```
actatcagag gtagttggcg tcatcgagcg ccatctcgaa ccgacgttgc tggccgtaca      960
tttgtacggc tccgcagtgg atggcggcct gaagccacac agtgtatattg atttgctggt   1020
tacggtgacc gtaaggcttg atgaaacaac gcggcgagct ttgatcaacg acctttggga   1080
aacttcggct tccctggag agagcgagat tctccgcgct gtagaagtca ccattgttgt    1140
gcacgacgac atcattccgt ggcgttatcc agctaagcgc gaactgcaat ttggagaatg   1200
gcagcgcaat gacattcttg caggtatctt cgagccagcc acgatcgaca ttgatctggc   1260
tatcttgctg acaaaagcaa gagaacatag cgttgccttg gtaggtccag cggcggagga   1320
actctttgat ccggttcctg aacaggatct atttgaggcg ctaaatgaaa ccttaacgct   1380
atggaactcg ccgcccgact gggctggcga tgagcgaaat gtagtgctta cgttgtcccg   1440
catttggtac agcgcagtaa ccggcaaaat cgcgccgaag gatgtcgctg ccgactgggc   1500
aatggagcgc ctgccggccc agtatcagcc cgtcatactt gaagctagac aggcttatct   1560
tggacaagaa gaagatcgct tggcctcgcg cgcagatcag ttggaagaat tgtccacta   1620
cgtgaaaggc gagatcacca agtagtcgg caaataatgt ctagctagat aacttcgtat   1680
aatgtatgct atacgaagtt atagacatta gcagataaat tagcaggaaa taagaagga   1740
taaggagaaa gaactcaagt aattatcctt cgttctctta attgaattgc aattaaactc   1800
ggcccaatct tttactaaaa ggattgagcc gaatacaaca aagattctat tgcatatatt   1860
ttgactaagt atatacttac ctagatatac aagatttgaa atacaaaatc tagcaagctt   1920
```

<210> SEQ ID NO 4
<211> LENGTH: 302
<212> TYPE: DNA
<213> ORGANISM: Artificial Sequence
<220> FEATURE:
<223> OTHER INFORMATION: Synthetic Sequence

<400> SEQUENCE: 4

```
ctcgagcaat cgccctgggt gggttacacg acgcccctct atggcccgta ctgacggaca     60
caccgaagcc ccggcggcaa ccctcagcgg atgccccggg gcttcacgtt tcccaggtc    120
agaagcggtt ttcgggagta gtgccccaac tggggtaacc tttgagttct ctcagttggg   180
ggcgtagggt cgccgacatg acacaagggg ttgtgaccgg gaagcttgat atcgaattcc   240
tgcagccgcg gtgcgggtgc cagggcgtgc ccttgggctc cccggggcgcg tactccacta   300
gt                                                                  302
```

<210> SEQ ID NO 5
<211> LENGTH: 28
<212> TYPE: DNA
<213> ORGANISM: Artificial Sequence
<220> FEATURE:
<223> OTHER INFORMATION: Recognition Site

<400> SEQUENCE: 5

```
ggtgcgcata atgtatatta tgttaaat                                       28
```

<210> SEQ ID NO 6
<211> LENGTH: 34
<212> TYPE: DNA
<213> ORGANISM: Artificial Sequence
<220> FEATURE:
<223> OTHER INFORMATION: Recognition Site

<400> SEQUENCE: 6

```
gaagttccta ttctctagaa agtataggaa cttc                                34
```

```
<210> SEQ ID NO 7
<211> LENGTH: 25
<212> TYPE: DNA
<213> ORGANISM: Artificial Sequence
<220> FEATURE:
<223> OTHER INFORMATION: Recognition Site

<400> SEQUENCE: 7
ttcttgaaaa ccaaggtttt tgata                                         25

<210> SEQ ID NO 8
<211> LENGTH: 26
<212> TYPE: DNA
<213> ORGANISM: Artificial Sequence
<220> FEATURE:
<223> OTHER INFORMATION: Recognition Site

<400> SEQUENCE: 8
ttatcaaaaa ccttccaaaa ggaaaa                                        26

<210> SEQ ID NO 9
<211> LENGTH: 50
<212> TYPE: DNA
<213> ORGANISM: Artificial Sequence
<220> FEATURE:
<223> OTHER INFORMATION: Recognition Site

<400> SEQUENCE: 9
agttgcccat gaccatgccg aagcagtggt agaagggcac cggcagacac              50

<210> SEQ ID NO 10
<211> LENGTH: 64
<212> TYPE: DNA
<213> ORGANISM: Artificial Sequence
<220> FEATURE:
<223> OTHER INFORMATION: Recognition Site

<400> SEQUENCE: 10
gcatgttccc caaagcgata ccacttgaag cagtggtact gcttgtgggt acactctgcg   60
ggtg                                                                64

<210> SEQ ID NO 11
<211> LENGTH: 80
<212> TYPE: DNA
<213> ORGANISM: Artificial Sequence
<220> FEATURE:
<223> OTHER INFORMATION: Recognition Site

<400> SEQUENCE: 11
accagagata gggcttatgc ataaaaaaat aagcccgtgt aagggagatt acacaggcta   60
aggaggtggt tcctggtaca                                               80

<210> SEQ ID NO 12
<211> LENGTH: 80
<212> TYPE: DNA
<213> ORGANISM: Artificial Sequence
<220> FEATURE:
<223> OTHER INFORMATION: Recognition Site

<400> SEQUENCE: 12
ttttatttca atttattgta cgtaaaaaat aagcccgtgt aagggagatt tagggtgtca   60
ccagtagggg ctttcaacgg                                               80
```

```
<210> SEQ ID NO 13
<211> LENGTH: 41
<212> TYPE: DNA
<213> ORGANISM: Artificial Sequence
<220> FEATURE:
<223> OTHER INFORMATION: Recognition Site

<400> SEQUENCE: 13
tccgttgaag cctgctttt tatactaact tgagcgaaac g                   41

<210> SEQ ID NO 14
<211> LENGTH: 51
<212> TYPE: DNA
<213> ORGANISM: Artificial Sequence
<220> FEATURE:
<223> OTHER INFORMATION: Recognition Site

<400> SEQUENCE: 14
cgtttctcgt tcagcttttt tatactaagt tggcattata aaaaagcatt g       51

<210> SEQ ID NO 15
<211> LENGTH: 81
<212> TYPE: DNA
<213> ORGANISM: Artificial Sequence
<220> FEATURE:
<223> OTHER INFORMATION: Recognition Site

<400> SEQUENCE: 15
gaagggcccg gaaccttgcg attccgggcc cttcttagtg gcgaggagta cgggacttga   60
acccgtggcc tccggcgtga c                                       81

<210> SEQ ID NO 16
<211> LENGTH: 81
<212> TYPE: DNA
<213> ORGANISM: Artificial Sequence
<220> FEATURE:
<223> OTHER INFORMATION: Recognition Site

<400> SEQUENCE: 16
aaaaccccag caagtccgag aacttgctgg ggcaggggtg gcgaggagta cgggacttga   60
acccgtactc ctgggctcct t                                       81

<210> SEQ ID NO 17
<211> LENGTH: 92
<212> TYPE: DNA
<213> ORGANISM: Artificial Sequence
<220> FEATURE:
<223> OTHER INFORMATION: Recognition Site

<400> SEQUENCE: 17
attacagctt aacctgacct aatgaagaaa ataaattgtt acacttctta ggaggagaag   60
tttcgatcag tcacctatat ctagttcaaa tt                           92

<210> SEQ ID NO 18
<211> LENGTH: 92
<212> TYPE: DNA
<213> ORGANISM: Artificial Sequence
<220> FEATURE:
<223> OTHER INFORMATION: Recognition Site

<400> SEQUENCE: 18
ccctatagca ctattgctac agggctttat ttattgctct acacttctta ggaggttcaa   60
tgtgacgaag tcacaccaat gttgatatta aa                           92
```

US 8,841,511 B2

REMOVAL OF PLASTID SEQUENCES BY TRANSIENTLY EXPRESSED SITE-SPECIFIC RECOMBINASES

This application is a §371 application of PCT/US04/06492 filed Mar. 3, 2004, which in turn claims priority to Provisional Applications 60/451,779 and 60/535,069 filed Mar. 3, 2003 and Jan. 8, 2004, respectively. Each of the above identified applications is incorporated by reference herein.

Pursuant to 35 U.S.C. §202(c) it is acknowledged that the U.S. Government has certain rights in the invention described, which was made in part with funds from the National Science Foundation Eukaryotic Genetics Program, Grant Number, MCB-0319958.

FIELD OF THE INVENTION

This invention relates to the fields of molecular biology and transgenic plants. More specifically, the invention provides nucleic acid constructs and methods of use thereof for removing sequences of interest using transiently expressed site-specific recombinases.

BACKGROUND OF THE INVENTION

Several publications and patent documents are cited throughout this application in order to better describe the state of the art to which this invention pertains. Each of these citations is incorporated by reference herein.

Engineering the plastid genome (ptDNA) rather than the nuclear genome gives rise to high protein expression levels and facilitates transgene containment. Plastid transformation involves targeted insertion of the transforming DNA into the plastid genome (ptDNA) by homologous recombination and amplification of the rare, transformed copies by selection for antibiotic resistance encoded in the vector (Bock, 2001; Staub, 2002; Maliga, 2004). Selection for vector-encoded antibiotic resistance genes is essential to obtain uniform transformation of the 1000 to 10000 ptDNA copies present in a higher plant. Following selection, continued expression of the selectable marker gene places an unnecessary metabolic burden on the plant, interferes with the need to use the same marker gene for multistep engineering and reduces consumer acceptance of the transgeneic plant. Thus, once transformation of ptDNA is accomplished, it is often desirable to eliminate the marker gene (Maliga, 2004).

Accordingly, it is an object of the invention to provide nucleic acid constructs and methods of use thereof for selective removal of predetermined sequences from the plastid genome.

SUMMARY OF THE INVENTION

In accordance with the present invention, compositions and methods are provided which facilitate the manipulation of the plastid genomes of higher plants. The methods of the invention may be employed to remove predetermined target sequences from the plastid genome, such as selectable marker genes following successful isolation of transformed progeny. Advantageously, the present inventors have developed methods and compositions wherein both the heterologous nucleic acids (encoding a selectable marker gene for example) and the recombinase are eliminated from the transplastomic plant cell, from which progeny plants producing a protein of interest can be regenerated.

In one embodiment of the invention, the method entails providing a transplastomic plant cell comprising plastids having heterologous nucleic acid sequence(s) flanked by excision sites and a nucleic acid sequence encoding at least one foreign gene of interest which is not flanked by excision sites. The plant cell is then contacted with a DNA construct which comprises a promoter operably linked to a nucleic acid encoding a protein having excision activity and optionally further comprises a sequence encoding a plastid transit peptide sequence and a selectable marker gene flanked by plant specific 5' and 3' regulatory regions under conditions where the DNA construct enters said cell and the proteins encoded thereby are transiently expressed for a suitable time period. The proteins catalyze the excision of the heterologous sequence from the plastids in the plant cell, thereby removing the heterologous sequence. Because the protein having excising activity is only transiently expressed, expression of this protein will also be lost. The method further entails identifying those transplastomic cells which lack both both the heterologous nucleic acid sequence and the protein having excising activity. In yet another embodiment, a progeny plant is generated from the plant cell following removal of the heterologous sequences.

Proteins having excision activity for use the practice of the present invention include, without limitation, CRE, flippase, resolvase, FLP, SSVI-encoded integrase, phiC31 integrase and transposases. Table I provides additional recombinase encoding sequences and excision sites recognized thereby.

In preferred embodiments, the heterologous nucleic acid encodes a selectable marker gene which confers resistance to a selection agent. Selection agents suitable for use in the present invention include spectinomycin, kanamycin, hygromycin, streptomycin, phophinotricin, basta, glyphosate, and bromxynil.

The constructs of the invention can be introduced into plant cells using a variety of methods, which include, without limitation, Agroinfiltration, PEG fusion, biolistic delivery, CaPO4-mediated transfection, and electroporation. Preferably, agroinfiltration is used and the contruct is transiently expressed in the nucleus.

The methods of the present invention can be used to generate tranplastomic plant species which include for example, tobacco, rice, potato, maize, soybean, oil seed rape, cotton and wheat.

DETAILED DESCRIPTION OF THE INVENTION

I. Definitions

Figure 1:
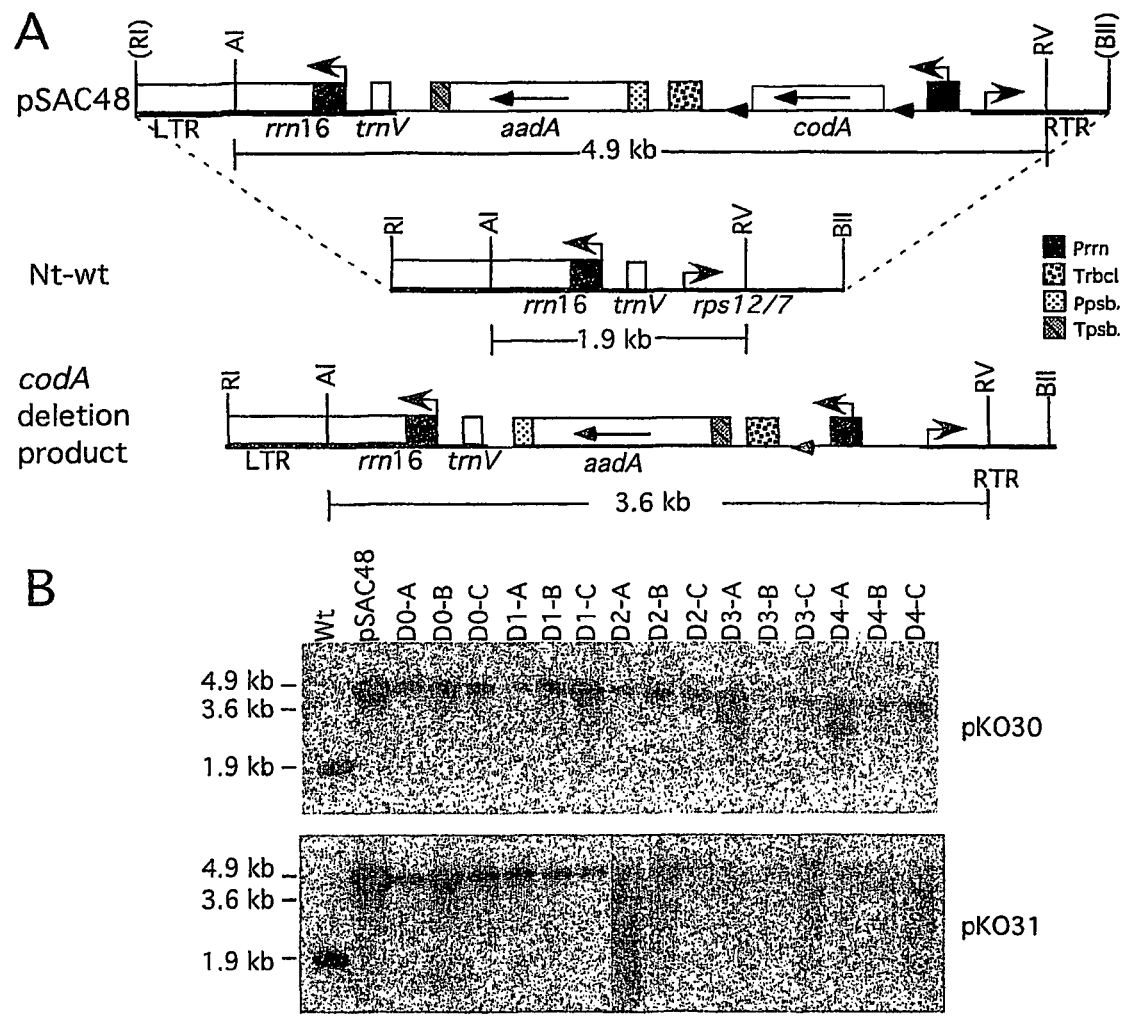
FIG. 1A shows a schematic diagram of plastid vector pSAC48 for CRE-mediated codA deletion. Shown are the plastid targeting region of vector pSAC48, the targeted region of the plastid genome (Nt-wt) and codA deletion derivative obtained by CRE-mediated recombination via lox sites. Positions of plastid genes rrn16, trnV and rps12/7 (Shinozaki et al., 1986), aadA and codA transgenes, lox-sites and relevant restriction sites (AI, ApaI; BII, BglII; RI, EcoRI; RV, EcoRV) are marked.
FIG. 1B shows DNA gel blot analysis tracking the codA deletion the first four days after Agroinfiltration. Total leaf cellular DNA was digested with the ApaI and EcoRV restriction endonucleases and probed with the targeting region (rrn16, 1.9-kb ApaI-EcoRV fragment). Fragments detected by the probing are marked in FIG. 1A.

The following definitions are provided to aid in understanding the subject matter regarded as the invention.

Heteroplastomic refers to the presence of a mixed population of different plastid genomes within a single plastid or in a population of plastids contained in plant cells or tissues.

Homoplastomic refers to a pure population of plastid genomes, either within a plastid or within a population contained in plant cells and tissues. Homoplastomic plastids, cells or tissues are genetically stable because they contain only one type of plastid genome. Hence, they remain homoplastomic even after the selection pressure has been removed, and selfed progeny are also homoplastomic. For purposes of the present invention, heteroplastomic populations of genomes that are functionally homoplastomic (i.e., contain only minor populations of wild-type DNA or transformed genomes with sequence variations) may be referred to herein as "functionally homoplastomic" or "substantially homoplastomic." These types of cells or tissues can be readily purified to a homoplastomic state by continued selection.

Plastome refers to the genome of a plastid.

Transplastome refers to a transformed plastid genome.

Transformation of plastids refers to the stable integration of transforming DNA into the plastid genome that is transmitted to the seed progeny of plants containing the transformed plastids. Alternatively, transformation may also include the introduction and transient expression of heterologous DNA into the plastid or nuclear genomes.

Selectable marker gene refers to a gene that upon expression confers a phenotype by which successfully transformed plastids or cells or tissues carrying the transformed plastid can be identified.

Transforming DNA refers to homologous DNA, or heterologous DNA flanked by homologous DNA, which when introduced into plastids becomes part of the plastid genome by homologous recombination.

An alternative type of transforming DNA refers to a DNA which contains recombination site sequences for a site-specific recombinase or integrase. Insertion of this type of DNA is not dependent of the degree of homology between the transforming DNA and the plastid to be transformed but rather is catalyzed by the action of the recombinase or integrase on the first and second recombination sites.

Operably linked refers to two different regions or two separate genes spliced together in a construct such that both regions will function to promote gene expression and/or protein translation.

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An isolated nucleic acid (either DNA or RNA) may further represent a molecule produced directly by biological or synthetic means and separated from other components present during its production.

The term "functional" as used herein implies that the nucleic or amino acid sequence is functional for the recited assay or purpose.

The phrase "consisting essentially of" when referring to a particular nucleotide or amino acid means a sequence having the properties of a given SEQ ID No:. For example, when used in reference to an amino acid sequence, the phrase includes the sequence per se and molecular modifications that would not affect the basic and novel characteristics of the sequence.

A "vector" is a replicon, such as a plasmid, cosmid, bacmid, phage or virus, to which another genetic sequence or element (either DNA or RNA) may be attached so as to bring about the replication of the attached sequence or element. Vectors, expression cassettes and methods suitable for the generation of transplastomic plants are described in U.S. Pat. Nos. 6,624,296, 6,472,586, 6,388,168, 6,376,744, 6,297,054, 5,877,402, and 5,451,513, by Maliga et al., the disclosures of which are incorporated by reference herein.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the production of a polypeptide coding sequence in a host cell or organism. Such expression signals may be combined such that production of said polypeptide occurs transiently or is produced stably over the life of the cell.

The term "oligonucleotide," as used herein refers to primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield an primer extension product. The primer may vary in length depending on the particular conditions and requirement of the application.

Amino acid residues described herein are preferred to be in the "L" isomeric form. However, residues in the "D" isomeric form may be substituted for any L-amino acid residue, provided the desired properties of the polypeptide are retained.

All amino-acid residue sequences represented herein conform to the conventional left-to-right amino-terminus to carboxy-terminus orientation The term "tag," "tag sequence" or "protein tag" refers to a chemical moiety, either a nucleotide, oligonucleotide, polynucleotide or an amino acid, peptide or protein or other chemical, that when added to another sequence, provides additional utility or confers useful properties, particularly in the detection or isolation, to that sequence. Thus, for example, a homopolymer nucleic acid sequence or a nucleic acid sequence complementary to a capture oligonucleotide may be added to a primer or probe sequence to facilitate the subsequent isolation of an extension product or hybridized product. In the case of protein tags, histidine residues (e.g., 4 to 8 consecutive histidine residues) may be added to either the amino- or carboxy-terminus of a protein to facilitate protein isolation by chelating metal chromatography. Alternatively, amino acid sequences, peptides, proteins or fusion partners representing epitopes or binding determinants reactive with specific antibody molecules or other molecules (e.g., flag epitope, c-myc epitope, transmembrane epitope of the influenza A virus hemaglutinin protein, protein A, cellulose binding domain, calmodulin binding protein, maltose binding protein, chitin binding domain, glutathione S-transferase, and the like) may be added to proteins to facilitate protein isolation by procedures such as affinity or immunoaffinity chromatography. Chemical tag moieties include such molecules as biotin, which may be added to either nucleic acids or proteins and facilitates isolation or detection by interaction with avidin reagents, and the like. Numerous other tag moieties are known to, and can be envisioned by, the trained artisan, and are contemplated to be within the scope of this definition.

As used herein, the terms "reporter," "reporter system", "reporter gene," or "reporter gene product" shall mean an operative genetic system in which a nucleic acid comprises a gene that encodes a product that when expressed produces a reporter signal that is a readily measurable, e.g., by biological assay, immunoassay, radioimmunoassay, or by calorimetric, fluorogenic, chemiluminescent or other methods. The nucleic acid may be either RNA or DNA, linear or circular, single or double stranded, antisense or sense polarity, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, polyA addition signals, transcriptional termination signals and the like. The terms "transform", "transfect", "transduce", shall refer to any method or means by which a nucleic acid is introduced into a cell or host organism and may be used interchangeably to convey the same meaning. Such methods include, but are not limited to, transfection, electroporation, microinjection, PEG-fusion, biolistic bombardment and the like.

"Agroinfiltration" refers to Agrobacterium mediated DNA transfer. Specifically, this process involves vacuum treatment of leaf segments in an Agrobacterium suspension and a subsequent release of vacuum which facilitates entry of bacterium cells into the iner-cellular space.

"T-DNA" refers to the transferred-region of the Ti (tumor-inducing) plasmid of Agrobacterium tumefaciens. Ti plasmids are natural gene transfer systems for the introduction of heterologous nucleic acids into the nucleus of higher plants. Binary Agrobacterium vectors such pBIN20 and pPZP22 (GenBank Accession Number 10463) are known in the art.

A "plastid transit peptide" is a sequence which, when linked to the N-terminus of a protein, directs transport of the protein from the cytoplasm to the plastid.

A "clone" or "clonal cell population" is a population of cells derived from a single cell or common ancestor by mitosis.

A "cell line" is a clone of a primary cell or cell population that is capable of stable growth in vitro for many generations.

II. Removal of Predetermined Target Sequences from the Plastids of Transgenic Plants The plastid genetic system is highly polyploid, as there are as many as 10,000 genome copies in a leaf cell. Plastid transformation is facilitated by selective amplification of the rare, transformed copies. This present invention addresses the reverse process, removal of the marker gene. This has been accomplished in the past by employing a site-specific recombinase, which has been stably incorporated in the nuclear genome. Since the recombinase gene is present in the nucleus and is constitutively expressed, there is ample time for the excision of all marker gene copies to take place. An alternative approach is described herein where excision function is obtained from transient expression of the site-specific recombinase. Excision of the marker genes by a transiently expressed recombinase in the absence of any selection resulted in the successful elimination of all copies from the plastid genome within a very short period of time. Thus, the method has the advantage of also eliminating the recombinase without resorting to segregation of seed progeny for this purpose.

Efficient protocols for marker gene excision rely on a CRE site-specific recombinase which excises marker genes flanked by directly-oriented, 34-bp loxP sites (floxed)(Corneille et al., 2001; Hajdukiewicz et al., 2001). CRE is fused with a plastid targeting sequence at its N-terminus, and is expressed from a stably integrated nuclear gene. After excision, Cre is removed from the nucleus by segregation in the seed progeny.

Providing CRE from a nuclear Cre gene facilitates efficient removal of the selectable marker gene, however stable expression of the CRE gene in progeny plants is undesirable. In accordance with the present invention, *Agrobacterium tumefaciens*-mediated transient gene expression or Agroinfiltration has been employed to provide, high, yet transient levels, of nuclear gene expression of recombinases, such as CRE, from a transiently introduced T-DNA region. It has been previously reported that histochemical staining after Agroinfiltration showed transgene-expressing sectors comprising up to 90% of the leaf area (Kapila et al., 1997). Additionally, this system is suitable for the delivery of multiple proteins carried on multiple *Agrobacterium* binary vectors (for example (Goodin et al., 2002)) and protein yields may be enhanced by suppression of RNA silencing (Johansen and Carrington, 2001). Finally, it is known that the T-region rarely integrates in the nucleus.

In accordance with the present invention, a P1 bacteriophage CRE-loxP site-specific recombination system is also provided which is suitable for efficient elimination of marker genes from the plastid genome by transiently expressing CRE from an introduced T-DNA region shown in Examples I and II. However, the utility of the system is not limited to the CRE-loxP system. Example III describes excision of marker genes by the phiC31 phage integrase via directly oriented attP and attB sites. There are many additional site-specific recombinases, which would be equally suitable for this application (Smith and Thorpe, 2002). See Table I. Advantageously, transient CRE expression significantly shortens the time required for selectable marker gene excision and enables applications in crops in which variety preservation is incompatible with seed propagation.

The following examples are provided to illustrate certain embodiments of the invention. They are not intended to limit the invention in any way.

EXAMPLE I

Removal of codA from the Plastid Genome by Agroinfiltration

The previously described CRE-loxP test system has two components: a plastid tester strain carrying a cytosine deaminase (codA) transgene flanked by lox sites (floxed) conferring sensitivity to 5-fluorocytosine (Nt-pSAC48 plant line) and a nuclear CRE line carrying a nuclear-encoded, plastid-targeted CRE (Nt-Cre1-100 and Nt-Cre2-300). Both the plastid tester (no CRE activity) and the nuclear CRE line (no lox sequence) were genetically stable. However, codA was eliminated at a very fast rate when the plastid-targeted CRE was introduced into the plastid tester strain by transformation or crossing. The gene for the nuclear-encoded CRE was subsequently separated from the transformed plastids by segregation in the seed progeny. This approach, i.e., removal of plastid sequences by CRE expressed from a stably integrated gene has been described in PCT/US00/25930 and in Corneille et al., 2001. This PCT application also provides T-DNA constructs for expressing recombinases such as CRE. PCT/US02/09537 also provides T-DNA constructs for expressing integrase.

To avoid the need to eliminate CRE expression via segregation in seed progeny, marker gene elimination by transient expression of CRE was assessed. Leaf segments of Nt-pSAC48 plants (1 cm$^2$) were placed in vacuum in an *Agrobacterium* suspension in which T-DNA transfer has been induced with acetosyringone as described (Kapila et al., 1997). *Agrobacterium* containing pKO30 (P2'long:TP5:cre:Tnos) or pKO31 (P2'long:TP22:cre:Tnos) (Corneille et al., 2001) were inoculated into 100 ml YEB medium with 100 µg/mL spectinomycin and grown overnight at 27° C. 1 ml from the above culture was inoculated into fresh YEB medium containing 10 µM MES 2-(N-morpholino)ethanesulfonic acid, pH adjusted to 5.6, 20 µM acetosyringone, and 100 µg/mL spectinomycin, and grown overnight at 27° C. The culture was centrifuged and resuspended in MMA medium to a final OD$_{660}$=2.4 as described in Kapila et al., 1997. After incubation at room temperature for 1 hour, vacuum infiltration was performed. Leaves were cut into small pieces (1 cm$^2$) and mixed with the *Agrobacterium* culture. The mixture was placed under continuous vacuum of 2 Torr for 20 minutes while shaking gently. Upon releasing the vacuum, the *Agrobacterium* suspension infiltrated the leaves.

For two days, the leaves were incubated on an antibiotic-free medium to allow T-DNA transfer by *Agrobacterium* into the tobacco nuclei. After two days, the leaves were transferred onto RMOP medium containing carbenicillin (500 mg/L) to kill *Agrobacterium*. Notably, no selection for the antibiotic resistance marker gene carried on the T-DNA was employed. Removal of codA from the plastid genome was tested in the infiltrated leaf segments during the first four days after Agroinfection, and in plants regenerated from the leaves.

Initially, elimination of codA was assessed during the first four days after Agroinfiltration. Three leaf pieces were collected daily and DNA was extracted to test for codA excision using the plastid-targeting region as the probe (FIG. 1). DNA gel blot analysis revealed that by day 3 codA was excised in ~50% of the plastid genome copies in three of the six samples; and by day 4 in four of the six leaf segments. Lack of excision in a small proportion of the day 4 samples is likely due to a lack in the uniformity of Agroinfiltration. Proteins introduced on the *Agrobacterium* T-DNA are expected to be expressed highly only for a few days. It was important, therefore, that deletion of codA occurred in 50% of the genome copies in this time frame suggesting that a significant fraction of regenerated plants will have the codA deleted.

Subsequently, codA excision in regenerated plants was tested. For this, shoots from the leaf sections were regenerated in the absence of selection for *Agrobacterium*-mediated T-DNA transfer by antibiotic resistance. Excision of codA was tested by DNA gel blot analysis of total cellular DNA isolated from leaves. To ensure independent, clonal origin of the plants, the infiltrated leaf samples (25 times 1 cm$^2$ each) were further subdivided (about 9 segments each), and only one regenerated plant was studied per piece.

Figure 2:
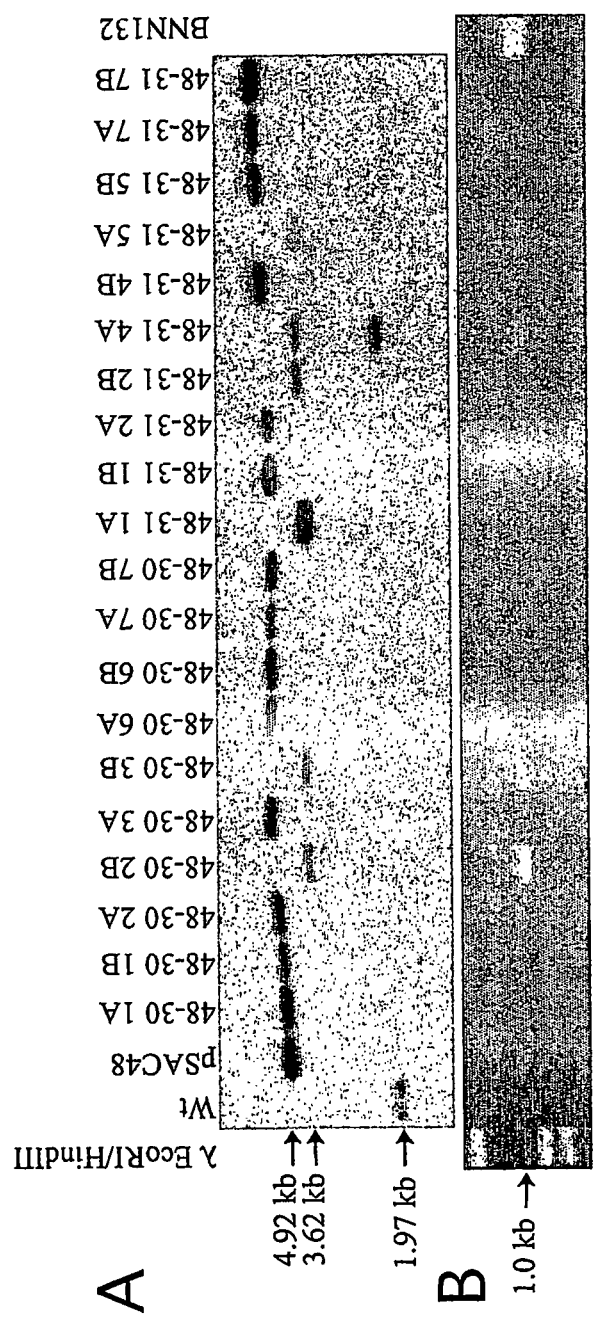
FIG. 2A shows DNA gel blot analysis testing CRE-mediated codA deletion in plants regenerated from Agroinfiltrated leaves. Total leaf cellular DNA was digested with the ApaI and EcoRV restriction endonucleases and probed with the targeting region (rrn16, 1.9-kb ApaI-EcoRV fragment). Fragments detected by the probing are marked in FIG. 1A.
FIG. 2B. PCR amplification to probe for Cre in DNA samples which were analyzed for codA deletion as shown in FIG. 2A.

Excision of codA was studied in 20 independently regenerated plants (FIG. 2). Excision of the target sequence was seen in six plants: three were homoplastomic for the deletion event (48-30-2B, 48-30-3B, 48-31-2B); one had a minor fraction of unexcised copies (48-31-1A) and two were heteroplastomic, containing genomes with codA deletion and codA-aadA-trnV deletion (48-31-4A, 48-31-5A). PCR analyses were carried out to test for Cre integration. Cre was present in four of the six samples in which codA was excised. Two clones 48-31-1A and 48-31-2B), i.e., 10% of the regenerated plants lacked an integrated Cre gene as well as all or most of the codA sequences used for selection of transformed plastids.

EXAMPLE II

Figure 3A:
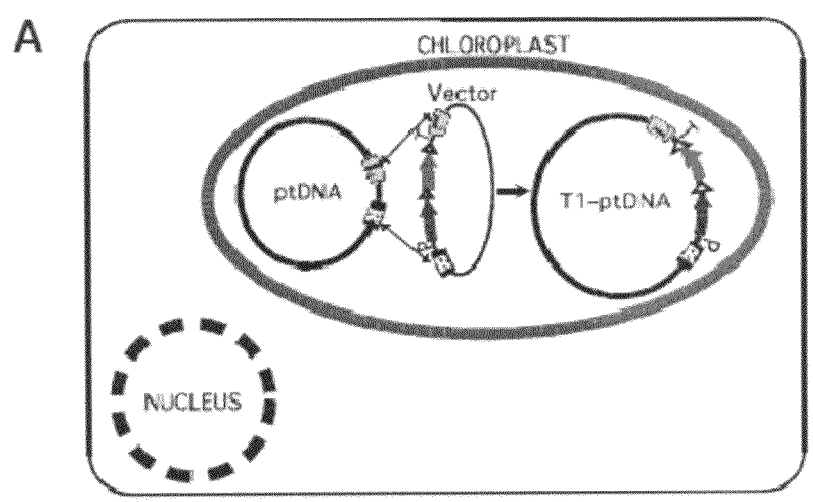
FIG. 3A is a schematic diagram showing the insertion of bar (dark arrow) and aadA (light arrow) genes into the plastid genome (ptDNA) by homologous recombination via left (L) and right (R) targeting sequences to obtain T1-ptDNA. Triangles represent lox sites.
Figure 3B:
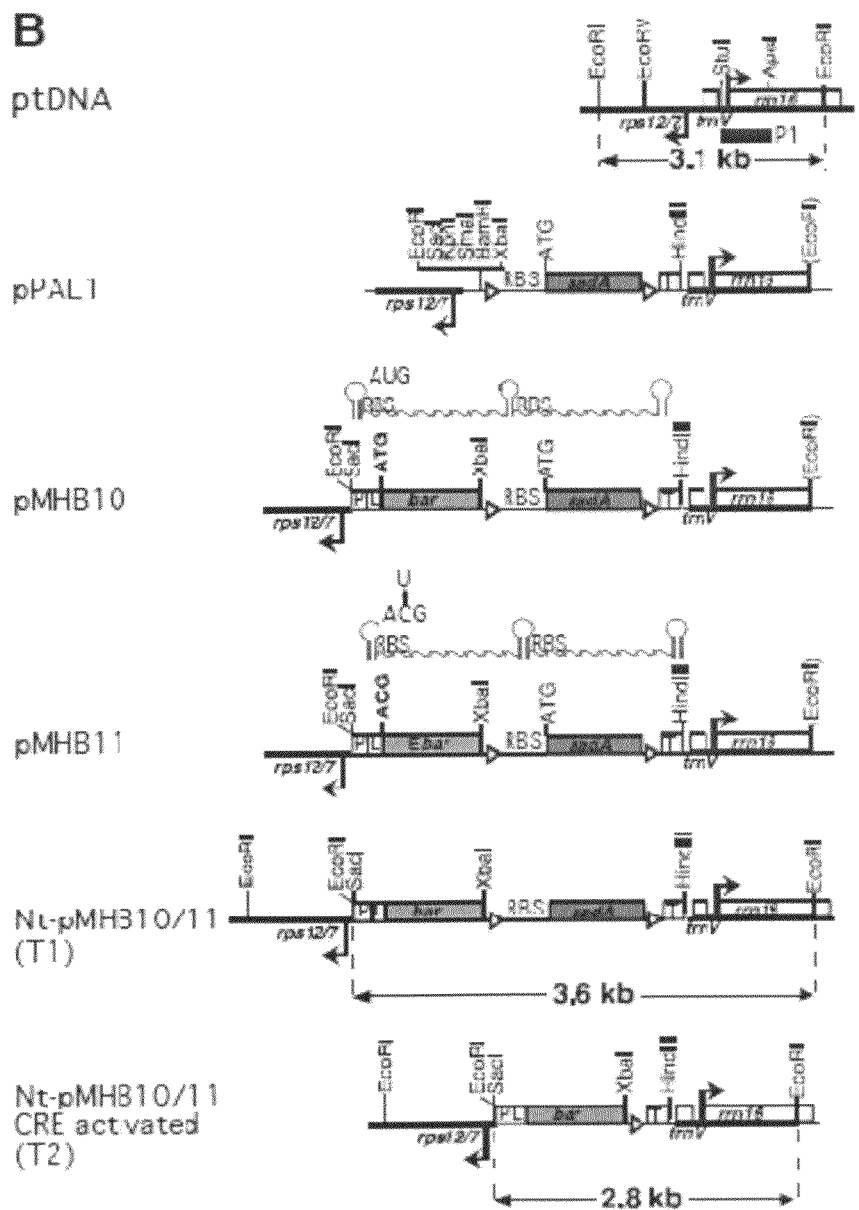
FIG. 3B depicts maps of ptDNA, plastid vectors pPAL1, pMHB10 and pMHB11, the T1-ptDNA of Nt-pMHB10 and Nt-pMHB11 plants, and of the T2-ptDNA after marker gene excision. Transcripts from vectors pMHB10 and pMHB11 with 5' and 3' stem-loop structures are shown in red above the maps. Abbreviations: rrn16, trnV and 3'-rps12/rps7 are plastid genes; RBS, ribosome binding site; PL, promoter-leader cassette; T, transcription terminator. Map distances and restriction enzyme recognition sites are marked.

Transiently Expressed Cre Yields Herbicide Resistant Transplastomic Tobacco Plants Free of Selectable Markers Construction of transplastomic herbicide resistant tobacco plants utilizing transient expression of recombinase is described in the present example. To test the efficiency of plastid marker gene excision with transiently expressed CRE, additional vectors were constructed which encode an herbicide resistance (bar) and a spectinomycin resistance (aadA) gene expressed from a single promoter by cloning a promoter-bar fragment into a promoter-less aadA/lox vector (pPAL1; FIG. 3B). The bar gene confers herbicide (phosphinothricin or PPT) resistance when the majority of ptDNA copies have been transformed, but is not suitable for direct selection of transplastomic clones when present in only a few of the 1,000 to 10,000 genome copies in a cell (Lutz et al., 2001; Ye et al., 2003). Linking bar to spectinomycin resistance (aadA) ensured efficient selection of transplastomic clones. The selectable aadA gene was floxed to facilitate its excision by the CRE. The bar genes encoded in vectors pMHB10 and pMHB11 differ in their leader sequence. Expression of the bar gene in plasmid pMHB11 is dependent on RNA editing (Ebar)(Chaudhuri and Maliga, 1996), a post-transcriptional event that converts an ACG codon (encoding a threonine) to an AUG translation initiation codon. In contrast, bar expression in plasmid pMHB10 is independent of RNA editing (FIG. 3B). Plasmid pPAL1 was obtained by replacing the EcoRI-HindIII region in plastid vector pPRV100B (Zoubenko et al., 1994) with a nucleic acid of SEQ ID NO: 1. Plasmid pMHB10 was obtained by replacing the EcoRI-HindIII region in plastid vector pPRV100B (Zoubenko et al., 1994) with a nucleic acid of SEQ ID NO: 2. Plasmid pMHB11 was obtained by replacing the EcoRI-HindIII region in plastid vector pPRV100B (Zoubenko et al., 1994) with a nucleic acid of SEQE ID NO:3.

Figure 3C:
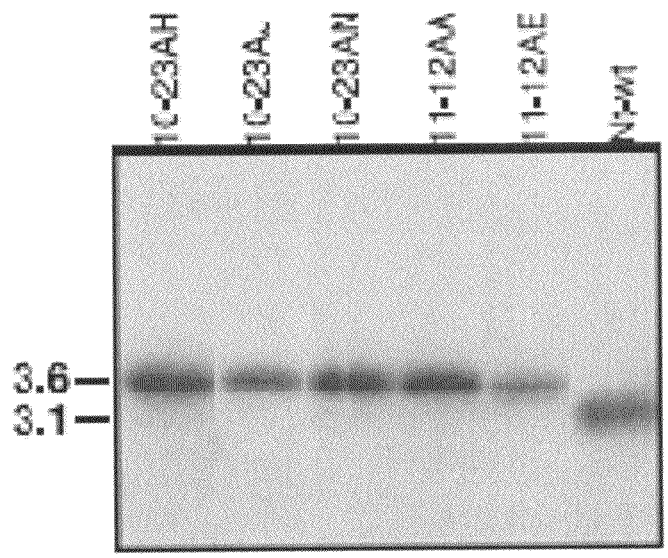
FIG. 3C shows DNA gel blot analysis to confirm T1-ptDNA structure in Nt-pMHB10 and Nt-pMHB11 transformed plants. Total leaf cellular DNA was digested with EcoRI and probed with the StuI/ApaI plastid DNA fragment (P1 probe, heavy line, FIG. 3B). The position and size of hybridizing fragments is marked in FIG. 3B.

Plasmids pMHB10 and pMHB11 were introduced into plastids by biolistic bombardment (Svab and Maliga, 1993), followed by integration of bar and aadA into the plastid genome, a process that yielded T1 transplastomes (T1-ptDNA; FIG. 3A). Transformed shoots were identified by spectinomycin resistance (500 mg/L) on a selective RMOP shoot regeneration medium (Svab and Maliga, 1993) and integration of the transforming DNA was verified by Southern blot analysis of total leaf cellular DNA (FIG. 3C). Plants were designated by plasmid name, a serial number and letters, for example Nt-pMHB10-23AH.

Figure 4:
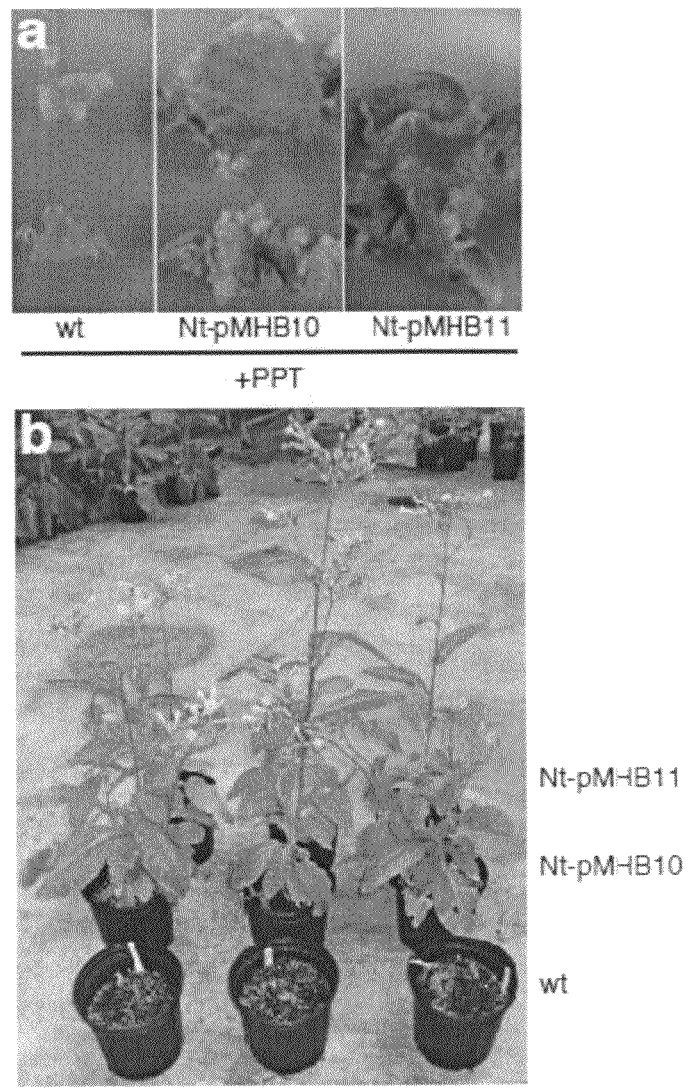
FIG. 4A shows that expression of Ebar confers herbicide resistance in a leaf assay of wt, Nt-pMHB10 and Nt-pMHB11 plants grown in the presence 4 mg/L of PPT.
FIG. 4B depicts wild-type (wt), Nt-pMHB10 and Nt-pMHB11 plants one month after spraying with Liberty (2%; AgrEvo, Wilmington, Del.).

T1-ptDNA plants were tested for herbicide resistance in cell culture and in the greenhouse. Leaf segments of both the Nt-pMHB10 and Nt-pMHB11 plants proliferated on a culture medium containing 4 mg/L phosphinothricin (PPT), the active compound of the herbicide Liberty, whereas the wild-type tobacco leaf segments bleached and died (FIG. 4A). Herbicide resistance was tested in the greenhouse by spraying (2% Liberty). The wild type plants died within two weeks, while the transgenic Nt-pMHB10 and Nt-pMHB11 plants flowered and set seed (FIG. 4B). The bar genes encode phosphinothricin acetyl transferase (PAT), an enzyme that detoxifies PPT. Acetylation of PPT was confirmed in leaf extracts of plants carrying the bar and Ebar genes. We also tested editing of the chimeric mRNA and found that >80% of the mRNAs had the ACG codon converted to an AUG translation initiation codon (data not shown). However, the editing-dependent Ebar gene (pMHB11) was not expressed in *E. coli*, as expected (Lutz et al., 2001)(data not shown), because prokaryotes lack the capacity for mRNA editing (Smith et al., 1997). Since no mRNA sequence is edited in the plant nucleus (Smith et al., 1997), Ebar mRNA will not confer herbicide resistance if the gene accidentally escapes to the plant nucleus (Huang et al., 2003; Stegemann et al., 2003). However, this Ebar will be expressed in the plastids of tobacco, and other higher plant species which share the capacity to edit the initiation codon of psbL mRNA (Kudla et al., 1992; Chateigner-Boutin and Hanson, 2002), the source of the edited segment (pSC4)(Chaudhuri et al., 1995). The editing-based herbicide-resistance gene described here is a useful alternative to intein-based protein splicing (Chin et al., 2003) and also provides an effective means of transgene containment.

Figure 5:
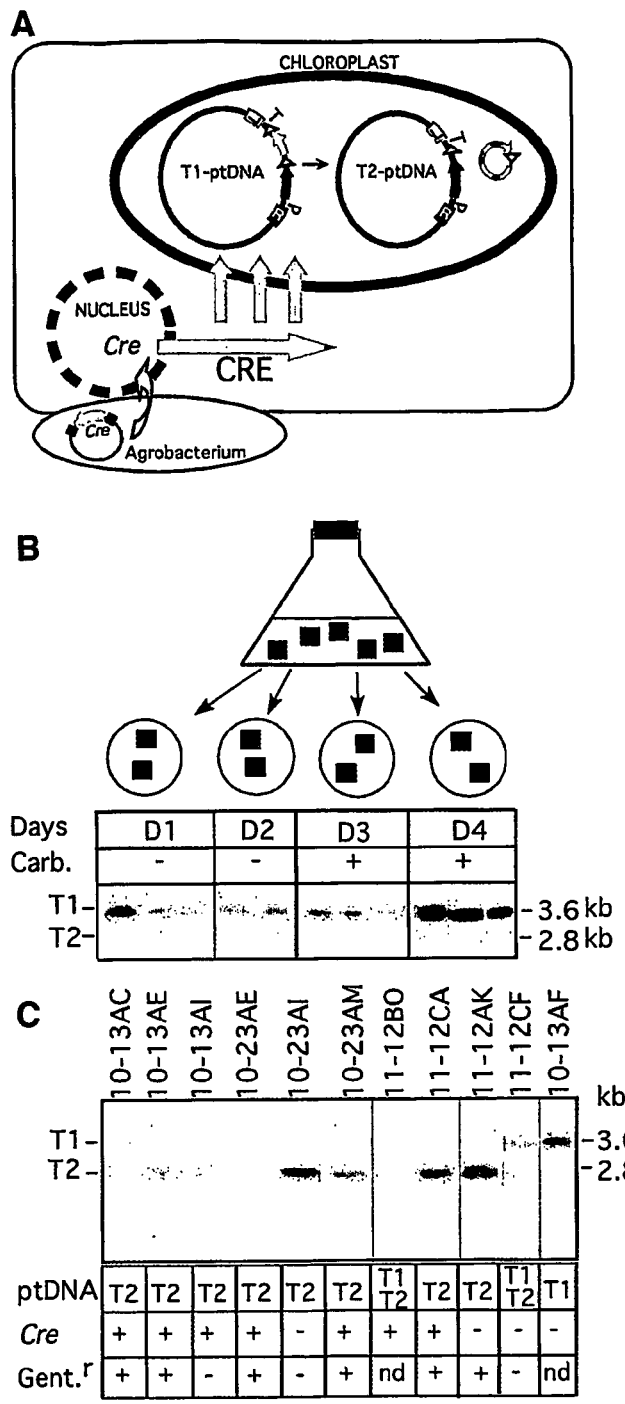
FIG. 5A shows excision of floxed aadA (light arrow) by transiently expressed CRE. Cre introduced into the plant nucleus on an *Agrobacterium* T-DNA is expressed in the cytoplasm, enters chloroplasts and excises floxed aadA from T1-ptDNA to yield T2-ptDNA. See Description of FIG. 3A.
FIG. 5B shows the results of short-term testing for excision. Vacuum infiltration of leaf disks (green squares) in *Agrobacterium* solution was followed by culture of leaf disks (1-4 days; D1-D4) on RMOP shoot regeneration medium (Svab and Maliga, 1993). Probing of EcoRI-digested total cellular DNA isolated from leaf disks with StuI/ApaI ptDNA fragment confirmed aadA excision: T1-ptDNA yields a 3.6-kb, T2-ptDNA a 2.8-kb diagnostic fragment (FIG. 3B). *Agrobacterium* was killed on day 3 by transferring leaf sections onto carbenicillin (500 mg/L) medium.
FIG. 5C shows the identification of T1 and/or T2 ptDNA in regenerated shoots by Southern blot analysis (for details see FIG. 5B). Information on Cre and the T-DNA plant marker gentamycin resistance (Gent$^r$) in the nucleus is listed below. Abbreviations: +, present; −, absent; nd, not determined.

According to the current protocols, the floxed marker gene is excised by CRE expressed from an integrated nuclear gene (Corneille et al., 2001; Hajdukiewicz et al., 2001). When tobacco plants with T1-ptDNA were obtained, we tested the feasibility of excising the floxed aadA marker gene from the plastid genome with a transiently expressed CRE (FIG. 5A). Based on the data presented in Example I, we anticipated that transient CRE expression would yield enough CRE to excise a significant fraction of the marker genes from the ~10,000 T1-ptDNA copies. Agroinfiltration has been previously described and is suitable for high-level nuclear gene expression from a transiently introduced T-DNA region. Agroinfiltration involves vacuum treatment of leaf segments in an *Agrobacterium* suspension, and subsequent release of the vacuum to facilitate entry of bacterium cells into the intercellular space (Kapila et al., 1997). Infiltration was performed with *Agrobacterium* strain EHA101 (Hood et al., 1986) carrying the pKO31 binary vector encoding a plastid-targeted CRE and gentamycin resistance as the plant marker (Corneille et al., 2003). Protein expressed from the T-DNA accumulates in two to four days after agroinfiltration (Johansen and Carrington, 2001; Voinnet et al., 2003). Therefore, we tested marker gene excision in T1-ptDNA leaf segments up to four days after agroinfiltration. Marker gene excision was observed as early as three days after agroinfiltration. By day four, a significant fraction of plastid genome copies lacked the marker gene (FIG. 5B).

Encouraged by the levels of marker gene excision in the short-term experiment, agroinfiltration was used in efforts to obtain marker-free transplastomic plants. Infiltration of Nt-pMHB10 and Nt-pMHB11 leaf sections was carried out with Agrobacterium EHA101 carrying vector pKO31 as described above. Two days after infiltration the leaf segments were placed on shoot regeneration medium, which contained carbenicillin (500 mg/L), to kill the Agrobacterium cells. Plants were then regenerated in the absence of selection for T-DNA transfer (gentamycin resistance). A month later the regenerated plants were individually tested for marker gene excision by Southern blot analysis (FIG. 5C). Marker-excised (T2) plastid genomes were detected in 19 of the 61 tested plants (11 of 27 Nt-pMHB10; 8 of 34 Nt-pMHB11). The nuclear Cre gene was absent in 7 clones (3 Nt-pMHB10; 4 Nt-pMHB11), as determined by PCR analysis (FIG. 5C). One of these (Nt-pMHB11-12AK) carries the unselected gentamycin resistance gene (data not shown).

Overall, excision of aadA by the transiently expressed nuclear CRE yielded marker-free transplastomic plants in ~10% (6 out of 61) of the regenerated plant's, in which Agrobacterium T-DNA delivery was not followed by T-DNA integration. This number is comparable to the ~12% excision frequency (13 out of 57) of a floxed plastid codA gene observed in regenerated shoots after agroinfiltration (See Example I) and is much higher than excision efficiency of a nuclear gene (0.25%) by a transiently expressed CRE in the absence of direct selection for the excision event (Gleave et al., 1999). For an overview of marker gene excision from the nuclear genome, see Hare and Chua, 2002 and Ow, 2002.

Presently four systems are available for plastid marker gene elimination. One approach relies on the loop-out of the marker gene through directly repeated sequences (Iamtham and Day, 2000). A second approach involves co-transformation with two independently targeted plastid transgenes (Ye et al., 2003). Both approaches are difficult to control since transformation and marker gene elimination occur simultaneously. The third approach is based on restoration of the green phenotype in pigment deficient mutants and depends on the availability of knockout mutants of plastid photosynthetic genes (Klaus et al., 2004). The most efficient, generally applicable approach excises floxed marker genes by CRE expressed from an integrated nuclear gene (Corneille et al., 2001; Hajdukiewicz et al., 2001). Plastid marker gene excision by transiently expressed CRE significantly accelerates the production of marker-free transplastomic plants as it eliminates the requirement to segregate out the nuclear Cre in the seed progeny. Until the present invention, CRE-mediated excision was not applicable to vegetatively propagated species such as potato, apple, and poplar, as variety preservation is incompatible with seed propagation in these highly heterozygous crops. Transient expression of CRE for marker gene removal now enables production of marker free transplastomic plants that belong to this group.

EXAMPLE III

Excision of Marker Genes by a Transiently Expressed phiC31 Phage Site-Specific Integrase (INT)

In addition to CRE-loxP, there are many site-specific recombination systems, which are suitable for the excision of plastid marker genes (Smith and Thorpe, 2002). One of these is the phiC31 phage integrase (INT), which mediates recombination between bacterial attB and phage attP sequences. The minimal sequences for attB and attP function were defined to be 34 and 39 bp, respectively (Groth et al., 2000). In mammalian cells longer sequences were more efficient. Therefore, in tobacco plastids, a 55-bp attB site was incorporated in the plastid genome to facilitate INT-mediated insertion of a vector carrying a 217-bp attP sequence (Lutz et al., 2004).

Figure 6:
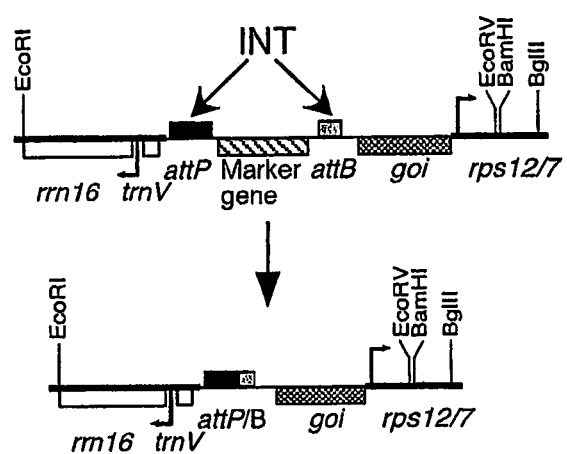
FIG. 6 depicts INT-mediated excision of an atted marker gene (upper) and the marker-free plastid genome (lower).
Figure 7:
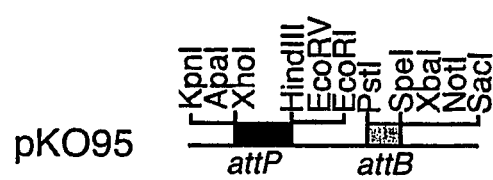
FIG. 7 shows directly oriented attP and attB sequences with restriction sites in pBluescriptKSII+ plasmid derivative pKO95.
Figure 8:
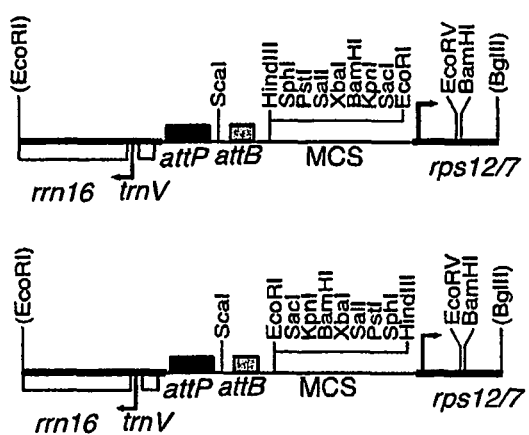
FIG. 8 provides schematic drawings of progenitor plasmids for construction of plastid transformation vectors with atted marker genes. Such vectors targeting insertions at the trnV-3'-rps12 intergenic region can be obtained by combining sequences from plastid vector pPRV1 described in U.S. Pat. No. 5,073,675, plasmid pKO95 and the marker genes cited in this application.

Molecular reactions carried out by the recombinase depend on the orientation and location (cis or trans) of target sequences. If the marker gene is flanked by directly orientated attB and attP target sites (atted), INT mediates excision of the atted marker gene and leaves behind a recombinant attB/attP site. A general scheme for a plastid vector with an atted marker gene is shown in FIG. 6. The atted marker gene can be excised by INT, which is stably integrated in the nucleus. Such stably transformed lines can be obtained by transformation with Agrobacterium binary vector pKO117 (Lutz et al., 2004). INT can also be expressed transiently by Agroinfiltration using binary vector pKO117 as described in Example II. To create a suitable plastid transformation vector containing an atted marker gene, attP and attB sequences from E. coli plasmid pKO95 can be used. The map of plasmid pKO95 is shown in FIG. 7; the DNA sequence of the region between the XhoI and SpeI sites is included within SEQ ID NO: 4. Plastid transformation vectors with an atted marker gene can be constructed using the progenitor plasmids shown in FIG. 8. Marker genes can be inserted at the Sca I site located between the directly oriented attP and attB sequences. Suitable marker genes for insertion have been described in U.S. Pat. No. 5,073,675 and pending patent application US99/17806. The multiple cloning sites are also present for cloning of passenger genes.

The following sequences were used in the methods of the present invention:

```
SEQ ID NO: 1
GAATTCGAGC TCGGTACCCG GGGATCCGGT ACatctagat GTACCATAAC
TTCGTATAAT GTATGCTATA CGAAGTTATa gatcaattca gttgtaggga
gggatttATG gGGGAAGCGG TGATCGCCGA AGTATCGACT CAACTATCAG
AGGTAGTTGG CGTCATCGAG CGCCATCTCG AACCGACGTT GCTGGCCGTA
CATTTGTACG GCTCCGCAGT GGATGGCGGC CTGAAGCCAC ACAGTGATAT
TGATTTGCTG GTTACGGTGA CCGTAAGGCT TGATGAAACA ACGCGGCGAG
CTTTGATCAA CGACCTTTTG GAAACTTCGG CTTCCCCTGG AGAGAGCGAG
ATTCTCCGCG CTGTAGAAGT CACCATTGTT GTGCACGACG ACATCATTCC
GTGGCGTTAT CCAGCTAAGC GCGAACTGCA ATTTGGAGAA TGGCAGCGCA
ATGACATTCT TGCAGGTATC TTCGAGCCAG CCACGATCGA CATTGATCTG
GCTATCTTGC TGACAAAAGC AAGAGAACAT AGCGTTGCCT TGGTAGGTCC
AGCGGCGGAG GAACTCTTTG ATCCGGTTCC TGAACAGGAT CTATTTGAGG
CGCTAAATGA AACCTTAACG CTATGGAACT CGCCGCCCGA CTGGGCTGGC
GATGAGCGAA ATGTAGTGCT TACGTTGTCC CGCATTTGGT ACAGCGCAGT
```

-continued
```
AACCGGCAAA ATCGCGCCGA AGGATGTCGC TGCCGACTGG GCAATGGAGC
GCCTGCCGGC CCAGTATCAG CCCGTCATAC TTGAAGCTAG ACAGGCTTAT
CTTGGACAAG AAGAAGATCG CTTGGCCTCG CGCGCAGATC AGTTGGAAGA
ATTTGTCCAC TACGTGAAAG GCGAGATCAC CAAGGTAGTC GGCAAATAAT
GTctagctag ataacttcgt ataatgtatg ctatacgaag ttatAGACAT
TAGCAGATAA ATTAGCAGGA AATAAAGAAG GATAAGGAGA AAGAACTCAA
GTAATTATCC TTCGTTCTCT TAATTGAATT GCAATTAAAC TCGGCCCAAT
CTTTTACTAA AAGGATTGAG CCGAATACAA CAAAGATTCT ATTGCATATA
TTTTGACTAA GTATATACTT ACCTAGATAT ACAAGATTTG AAATACAAAA
TCTAGcaagc tt SEQ ID NO: 2:
GAATTCGAGC TCGCTCCCCC GCCGTCGTTC AATGAGAATG GATAAGAGGC
TCGTGGGATT GACGTGAGGG GGCAGGGATG GCTATATTTC TGGGAGAATT
AACCGATCGA CGTGCaAGCG GACATTTATT TTaAATTCGA TAATTTTTGC
AAAAACATTT CGACATATTT ATTTATTTTA TTATTATGAG AATCAATCCT
ACTACTTCTG GTTCTGGGGT TTCCACGgct AGCCCAGAAa GAaGaCCGGC
CGACATCCGC CGTGCCACCG AGGCGGACAT GCCGGCGGTC TGCACCATCG
TCAACCACTA CATCGAGACA AGCACGGTCA ACTTCCGTAC CGAGCCGCAG
GAACCGCAGG AGTGGACGGA CGACCTCGTC CGTCTGCGGG AGCGCTATCC
CTGGCTCGTC GCCGAGGTGG ACGGCGAGGT CGCCGGCATC GCCTACGCGG
GCCCCTGGAA GGCACGCAAC GCCTACGACT GGACGGCCGA GTCGACCGTG
TACGTCTCCC CCCGCCACCA GCGGACGGGA CTGGGCTCCA CGCTCTACAC
CCACCTGCTG AAGTCCCTGG AGGCACAGGG CTTCAAGAGC GTGGTCGCTG
TCATCGGGCT GCCCAACGAC CCGAGCGTGC GCATGCACGA GGCGCTCGGA
TATGCCCCCC GCGGCATGCT GCGGGCGGCC GGCTTCAAGC ACGGGAACTG
GCATGACGTG GGTTTCTGGC AGCTGGACTT CAGCCTGCCG GTACCGCCCC
GTCCGGTCCT GCCCGTCACC GAGATCTGAT GAtctagatG TACCATAACT
TCGTATAATG TATGCTATAC GAAGTTATag atcaattcag ttgtagggag
ggatttATGg GGGAAGCGGT GATCGCCGAA GTATCGACTC AACTATCAGA
GGTAGTTGGC GTCATCGAGC GCCATCTCGA ACCGACGTTG CTGGCCGTAC
ATTTGTACGG CTCCGCAGTG GATGGCGGCC TGAAGCCACA CAGTGATATT
GATTTGCTGG TTACGGTGAC CGTAAGGCTT GATGAAACAA CGCGGCGAGC
TTTGATCAAC GACCTTTTGG AAACTTCGGC TTCCCCTGGA GAGAGCGAGA
TTCTCCGCGC TGTAGAAGTC ACCATTGTTG TGCACGACGA CATCATTCCG
TGGCGTTATC CAGCTAAGCG CGAACTGCAA TTTGGAGAAT GGCAGCGCAA
TGACATTCTT GCAGGTATCT TCGAGCCAGC CACGATCGAC ATTGATCTGG
CTATCTTGCT GACAAAAGCA AGAGAACATA GCGTTGCCTT GGTAGGTCCA
GCGGCGGAGG AACTCTTTGA TCCGGTTCCT GAACAGGATC TATTTGAGGC
GCTAAATGAA ACCTTAACGC TATGAACTC GCCGCCCGAC TGGGCTGGCG
ATGAGCGAAA TGTAGTGCTT ACGTTGTCCC GCATTTGGTA CAGCGCAGTA
ACCGGCAAAA TCGCGCCGAA GGATGTCGCT GCCGACTGGG CAATGGAGCG
CCTGCCGGCC CAGTATCAGC CCGTCATACT TGAAGCTAGA CAGGCTTATC
TTGGACAAGA AGAAGATCGC TTGGCCTCGC GCGCAGATCA GTTGGAAGAA
TTTGTCCACT ACGTGAAAGG CGAGATCACC AAGGTAGTCG GCAAATAATG
Tctagctaga taacttcgta taatgtatgc tatacgaagt tatAGACATT
AGCAGATAAA TTAGCAGGAA ATAAAGAAGG ATAAGGAGAA AGAACTCAAG
TAATTATCCT TCGTTCTCTT AATTGAATTG CAATTAAACT CGGCCCAATC
TTTTACTAAA AGGATTGAGC CGAATACAAC AAAGATTCTA TTGCATATAT
TTTGACTAAG TATATACTTA CCTAGATATA CAAGATTTGA AATACAAAAT
CTAGcaagct t SEQ ID NO: 3:
GAATTCgagc tcggtaccca aaGCTCCCCC GCCGTCGTTC AATGAGAATG
GATAAGAGGC TCGTGGGATT GACGTGAGGG GGCAGGGATG GCTATATTTC
TGGGAGCGAA CTCCGGGCGA ATACGAAGCG CTTGGATACA GTTGTAGGGA
GGGATCCATG gCTTTGGGAT CAATATCAGC AATGCAGTTC ATCCAACGAT
AAACTTAATC CGAATTATAG AGCTACGACA CAATCAgctA GCCCAGAAaG
AaGaCCGGCC GACATCCGCC GTGCCACCGA GGCGGACATG CCGGCGGTCT
GCACCATCGT CAACCACTAC ATCGAGACAA GCACGGTCAA CTTCCGTACC
GAGCCGCAGG AACCGCAGGA GTGGACGGAC GACCTCGTCC GTCTGCGGGA
GCGCTATCCC TGGCTCGTCG CCGAGGTGGA CGGCGAGGTC GCCGGCATCG
CCTACGCGGG CCCCTGGAAG GCACGCAACG CCTACGACTG GACGGCCGAG
TCGACCGTGT ACGTCTCCCC CCGCCACCAG CGGACGGGAC TGGGCTCCAC
GCTCTACACC CACCTGCTGA AGTCCCTGGA GGCACAGGGC TTCAAGAGCG
TGGTCGCTGT CATCGGGCTG CCCAACGACC CGAGCGTGCG CATGCACGAG
GCGCTCGGAT ATGCCCCCCG CGGCATGCTG CGGGCGGCCG GCTTCAAGCA
CGGGAACTGG CATGACGTGG GTTTCTGGCA GCTGGACTTC AGCCTGCCGG
TACCGCCCCG TCCGGTCCTG CCCGTCACCG AGATCTGATG AtctagatGT
ACCATAACTT CGTATAATGT ATGCTATACG AAGTTATaga tcaattcagt
tgtagggagg gatttATGgG GGAAGCGGTG ATCGCCGAAG TATCGACTCA
ACTATCAGAG GTAGTTGGCG TCATCGAGCC CCATCTCGAA CCGACGTTGC
TGGCCGTACA TTTGTACGGC TCCGCAGTGG ATGGCGGCCT GAAGCCACAC
AGTGATATTG ATTTGCTGGT TACGGTGACC GTAAGGCTTG ATGAAACAAC
GCGGCGAGCT TTGATCAACG ACCTTTTGGA AACTTCGGCT TCCCCTGGAG
AGAGCGAGAT TCTCCGCGCT GTAGAAGTCA CCATTGTTGT GCACGACGAC
ATCATTCCGT GGCGTTATCC AGCTAAGCGC GAACTGCAAT TTGGAGAATG
GCAGCGCAAT GACATTCTTG CAGGTATCTT CGAGCCAGCC ACGATCGACA
TTGATCTGGC TATCTTGCTG ACAAAAGCAA GAGAACATAG CGTTGCCTTG
GTAGGTCCAG CGGCGGAGGA ACTCTTTGAT CCGGTTCCTG AACAGGATCT
ATTTGAGGCG CTAAATGAAA CCTTAACGCT ATGGAACTCG CCGCCCGACT
```

```
                      -continued
GGGCTGGCGA TGAGCGAAAT GTAGTGCTTA CGTTGTCCCG CATTTGGTAC
AGCGCAGTAA CCGGCAAAAT CGCGCCGAAG GATGTCGCTG CCGACTGGGC
AATGGAGCGC CTGCCGGCCC AGTATCAGCC CGTCATACTT GAAGCTAGAC
AGGCTTATCT TGGACAAGAA GAAGATCGCT TGGCCTCGCG CGCAGATCAG
TTGGAAGAAT TTGTCCACTA CGTGAAAGGC GAGATCACCA AGGTAGTCGG
CAAATAATGT ctagctagat aacttcgtat aatgtatgct atacgaagtt
atAGACATTA GCAGATAAAT TAGCAGGAAA TAAAGAAGGA TAAGGAGAAA
GAACTCAAGT AATTATCCTT CGTTCTCTTA ATTGAATTGC AATTAAACTC
GGCCCAATCT TTTACTAAAA GGATTGAGCC GAATACAACA AAGATTCTAT
TGCATATATT TTGACTAAGT ATATACTTAC CTAGATATAC AAGATTTGAA
ATACAAAATC TAGcaagctt SEQ ID NO: 4:
ctcGAGCAAT CGCCCTGGGT GGGTTACACG ACGCCCTCT ATGGCCCGTA
CTGACGGACA CACCGAAGCC CCGGCGGCAA CCCTCAGCGG ATGCCCCGGG
GCTTCACGTT TTCCCAGGTC AGAAGCGGTT TTCGGGAGTA GTGCCCCAAC
TGGGGTAACC TTTGAGTTCT CTCAGTTGGG GGCGTAGGGT CGCCGACATG
ACACAAGGGG TTGTGACCGG Gaagcttgat atcgaattcc tgcAGCCGCG
GTGCGGGTGC CAGGGCGTGC CCTTGGGCTC CCCGGGCGCG TACTCCACta
gt
```

While the use of CRE and phi31 integrase recombinases are exemplified herein, other recombinases identified by GenBank accession numbers and their cognate excision site sequences are encompassed within the scope of the present invention and are set forth below in Table I.

TABLE 1

Site-specific recombinases and the corresponding recognition site and references

| Name | Rec. site | Recognition sequence | Ref. |
|---|---|---|---|
| XerC C37841 | dif | GGTGCGCATAATGTATATTATGTTA AAT *(5) | (Cornet et al., 1997) |
| XerD P21891 | dif | GGTGCGCATAATGTATATTATGTTA AAT (5) | (Cornet et al., 1997) |
| Flp J01347 | FRT | GAAGTTCCTATTCTCTAGAAAGTAT AGGAACTTC (6) | (Luetke and Sadowski, 1998) |
| Hin NCC_00 3197 | hixL | TTCTTGAAAACCAAGGTTTTTGATA (7) | (Glasgow et al., 1989) |
|  | hixR | TTATCAAAAACCTTCCAAAAGGAAAA (8) |  |
| R4 D90361 | attB | AGTTGCCCATGACCATGCCGAAGCAG TGGTAGAAGGGCACCGGCAGACAC (9) | (Olivares et al., 2001) |
|  | attP | GCATGTTCCCCAAAGCGATACCACTT GAAGCAGTGTACTGCTTGTGGGTAC ACTCTGCGGGTG (10) |  |
| P2 AAD03297 | attB | ACCAGAGATAGGGCTTATGCATAAAA AAATAAGCCCGTGTAAGGGAGATTAC ACAGGCTAAGGAGGTGGTTCCTGGTA CA (11) | (Yu et al., 1989) |
|  | attP | TTTTATTTCAATTTATTGTACGTAAA AAATAAGCCCGTGTAAGGGAGATTTA GGGTGTCACCAGTAGGGGCTTTCAAC GG (12) |  |
| lambda AAA96562 | attB | TCCGTTGAAGCCTGCTTTTTTATACT AACTTGAGCGAAACG (13) | (Ross et al., 1979) |
|  | attP | CGTTTCTCGTTCAGCTTTTTTATACT AAGTTGGCATTATAAAAAAGCATTG (14) |  |
| Mx8 AAC48895 | attB | GAAGGGCCCGGAACCTTGCGATTCCG GGCCCTTCTTAGTGGCGAGGAGTACG GGACTTGAACCCGTGGCCTCCGGCGT GAC (15) | (Tojo et al., 1996) |
| phiadh JN0535 | attB | ATTACAGCTTAACCTGACCTAATGAA GAAAATAAATTGTTACACTTCTTAGG AGGAGAAGTTTCGATCAGTCACCTAT ATCTAGTTCAAATT (17) | (Raya et al., 1992) |
|  | attP | CCCTATAGCACTATTGCTACAGGGCT TTATTTATTGCTCTACACTTCTTAGG AGGTTCAATGTGACGAAGTCACACCA ATGTTGATATTAAA (18) |  |

*Numbers in parenthesis correspond to SEQ ID NOS:

Cornet, F., Hallet, B. and Sherratt, D.J.: Xer recombination in *Escherichia coli*. Site-specific DNA topoisomerase activity of the XerC and XerD recombinases. The Journal of Biological Chemistry 272 (1997)21927-31.

Glasgow, A.C., Bruist, M.F. and Simon, M.I.: DNA-binding properties of the Hin recombinase. The Journal of Biological Chemistry 264 (1989)10072-82.

Luetke, K.H. and Sadowski, P.D.: DNA sequence determinant for Flp-induced DNA bending. Molecular Microbiology 29 (1998)199-208.

Olivares, E.C., Hollis, R.P. and Calos, M.P.: Phage R4 integrase mediates site-specific integration in human cells. Gene 278 (2001)167-76.

Raya, R.R., Fremaux, C., De_Antoni, G.L. and Klaenhammer, T.R.: Site-specific integration of the temperate bacteriophage phi adh into the *Lactobacillus gasseri* chromosome and molecular characterization of the phage (attP) and bacterial (attB) attachment sites. Journal of Bacteriology 174 (1992)5584-92.

Ross, W., Landy, A., Kikuchi, Y. and Nash, H.: Interaction of int protein with specific sites on lambda att DNA. Cell 18 (1979)297-307.

Tojo, N., Sanmiya, K., Sugawara, H., Inouye, S. and Komano, T.: Integration of bacteriophage Mx8 into the *Myxococcus xanthus* chromosome causes a structural alteration in the C-terminal region of the IntP protein. Journal of Bacteriology 178 (1996)4004-11.

Yu, A., Bertani, L.E. and Haggard_Ljungquist, E.: Control of prophage integration and excision in bacteriophage P2: nucleotide sequences of the int gene and att sites. Gene 80 (1989)1-11.

REFERENCES

Bock, R. (2001) Transgenic plastids in basic research and plant biotechnology. *J. Mol. Biol.* 312, 425-438.

Chateigner-Boutin, A. L. and Hanson, M. R. (2002) Cross-competition in transgenic chloroplasts expressing single editing sites reveals shared cis elements. *Mol. Cell. Biol.* 22, 8448-8456.

Chaudhuri, S. and Maliga, P. (1996) Sequences directing C to U editing of the plastid psbL mRNA are located within a 22 nucleotide segment spanning the editing site. *EMBO J.* 15, 5958-5964.

Chaudhuri, S., Carrer, H. and Maliga, P. (1995) Site-specific factor involved in the editing of the psbL mRNA in tobacco plastids. *EMBO J.* 14, 2951-2957.

Chin, H. H., Kim, G. D., Marin, I., Mersha, F., Evans, T. C., Chen, L., Xu, M. Q. and Pradhan, S. (2003) Protein trans-splicing in transgenic plant chloroplast: Reconstruction of herbicide resistance from split genes. *Proc. Natl. Acad. Sci. U.S.A.* 100, 4510-4515.

Corneille, S., Lutz, K., Svab, Z. and Maliga, P. (2001) Efficient elimination of selectable marker genes from the plastid genome by the CRE-lox site-specific recombination system. *Plant J.* 72, 171-178.

Corneille, S., Lutz, K. A., Azhagiri, A. K. and Maliga, P. (2003) Identification of functional lox sites in the plastid genome. *Plant J.* 35, 753-762.

Gleave, A. P., Mitra, D. S., Mudge, S. R. and Morris, B. A. (1999) Selectable marker-free transgenic plants without sexual crossing: transient expression of cre recombinase and use of a conditional lethal dominant gene. *Plant Mol. Biol.* 40, 223-235.

Goodin, M. M., Dietzgen, R. G., Schichnes, D., Ruzin, S. and Jackson, A. O. (2002) pGD vectors: versatile tools for the expression of green and red fluorescent protein fusions in agroinfiltrated plant leaves. *Plant J.* 31, 375-383.

Groth, A. C., Olivares, E. C., Thyagarajan, B. and Calos, M. P. (2000) A phage integrase directs efficient site-specific integration in human cells. *Proc. Natl. Acad. Sci. U.S.A.* 97, 5995-6000.

Hajdukiewicz, P. T. J., Gilbertson, L. and Staub, J. M. (2001) Multiple pathways for Cre/lox-mediated recombination in plastids. *Plant J.* 27, 161-170.

Hare, P. D. and Chua, N. H. (2002) Excision of selectable marker genes from transgenic plants. *Nat. Biotechnol.* 20, 575-580.

Hood, E. E., Helmer, G. L., Fraley, R. T. and Chilton, M. D. (1986) The hypervirulance of *Agrobacterium tumefaciens* A281 is encoded in a region of pTiBo542 outside of T-DNA. *J. Bacteriol.* 168, 1291-1301.

Huang, C. Y., Ayliffe, M. A. and Timmis, J. N. (2003) Direct measurement of the transfer rate of chloroplast DNA into the nucleus. *Nature* 422, 72-76.

Iamtham, S. and Day, A. (2000) Removal of antibiotic resistance genes from transgenic tobacco plastids. *Nat. Biotechnol.* 18, 1172-1176.

Johansen, L. K. and Carrington, J. C. (2001) Silencing on the spot. Induction and suppression of RNA silencing in the *Agrobacterium*-mediated transient expression system. *Plant Physiol.* 126, 930-938.

Kapila, J., De Rycke, R., Van Montagu, M. and Angenon, G. (1997) An *Agrobacterium*-mediated transient gene expression system for intact leaves. *Plant Sci.* 122, 101-108.

Klaus, S. M. J., Huang, F. C., Golds, T. J. and Koop, H.-U. (2004) Generation of marker-free plastid transformants using a transiently cointegrated selection gene. *Nat. Biotechnol.* 22, 225-229.

Kudla, J., Igloi, G. L., Metzlaff, M., Hagemann, R. and Kössel, H. (1992) RNA editing in tobacco chloroplasts leads to the formation of a translatable psbL mRNA by a C to U substitution within the initiation codon. *EMBO J.* 11, 1099-1103.

Lutz, K., Corneille, S., Azhagiri, A. K., Svab, Z. and Maliga, P. (2004) A novel approach to plastid transformation utilizes the phiC31 phage integrase. *Plant J.* in press.

Lutz, K. A., Knapp, J. E. and Maliga, P. (2001) Expression of bar in the plastid genome confers herbicide resistance. *Plant Physiol.* 125, 1585-1590.

Maliga, P. (2004) Plastid transformation in higher plants. *Annu. Rev. Plant Biol.* 55, 289-313.

Ow, D. W. (2002) Recombinase-directed plant transformation for the post-genomic era. *Plant Mol. Biol.* 48, 183-200.

Shinozaki, K., Ohme, M., Tanaka, M., Wakasugi, T., Hayashida, N., Matsubayashi, T., Zaita, N., Chunwongse, J., Obokata, J., Yamaguchi-Shinozaki, K., Ohto, C., Torazawa, K., Meng, B.-Y., Sugita, M., Deno, H., Kamogashira, T., Yamada, K., Kusuda, J., Takaiwa, F., Kato, A., Tohdoh, N., Shimada, H. and Sugiura, M. (1986) The complete nucleotide sequence of the tobacco chloroplast genome: its gene organization and expression. *EMBO J.* 5, 2043-2049.

Smith, H. C., Gott, J. M. and Hanson, M. R. (1997) A guide to RNA editing. *RNA* 3, 1105-1123.

Smith, M. C. M. and Thorpe, H. M. (2002) Diversity in the serine recombinases. *Mol. Microbiol.* 44, 299-307.

Staub, J. M. (2002) Expression of recombinant proteins via the plastid genome. In *Handbook of industrial cell culture: mammalian, microbial and plant cells.* (Parekh, S. R. and Vinci, V. A., eds). Totowa, N.J.: Humana Press Inc., pp. 261-280.

Stegemann, S., Hartmann, S., Ruf, S. and Bock, R. (2003) High-frequency gene transfer from the chloroplast genome to the nucleus. *Proc. Natl. Acad. Sci. U.S.A.* 100, 8828-8833.

Svab, Z. and Maliga, P. (1993) High-frequency plastid transformation in tobacco by selection for a chimeric aadA gene. *Proc. Natl. Acad. Sci. U.S.A.* 90, 913-917.

Voinnet, O., Rivas, S., Mestre, P. and Baulcombe, D. (2003) An enhanced transient expression system in plants based on supression of gene silencing by the p19 protein from tomato bushy stunt virus. *Plant J.* 33, 949-956.

Ye, G. N., Colburn, S., Xu, C. W., Hajdukiewicz, P. T. J. and Staub, J. M. (2003) Persistance of unselected transgenic DNA during a plastid transformation and segregation approach to herbicide resistance. *Plant Physiol.* 133, 402-410.

Zoubenko, O. V., Allison, L. A., Svab, Z. and Maliga, P. (1994) Efficient targeting of foreign genes into the tobacco plastid genome. *Nucleic Acids Res.* 22, 3819-3824.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A site specific recombination method for removal of heterologous nucleic acid sequences from the plastid genome, said method comprising:
   a) providing a transplastomic plant cell, said plastids of said cell comprising a heterologous nucleic acid sequence flanked by excision sites and a nucleic acid sequence encoding at least one foreign gene of interest which is not flanked by excision sites;
   b) providing a DNA construct, said construct comprising a promoter operably linked to a nucleic acid encoding a protein having excision activity on the excision sites of step a) said construct comprising a sequence encoding a plastid transit peptide sequence and a selectable marker gene flanked by plant specific 5' and 3' regulatory regions;
   c) introducing the construct of step b) into the plant cell of step a) such that said DNA construct enters said cell, but does not integrate into the nuclear genome of a plant cell, whereby the proteins encoded thereby are transiently expressed in said plant cell for a suitable time period, said proteins catalyzing the excision of the heterologous sequence from the plastids in the plant cell of step a), thereby removing said heterologous sequence; and
   d) regenerating a plant from the cell of step c) without previously selecting for the excision of the heterologous sequence, said plant lacking both said heterologous nucleic acid sequence and said protein having excising activity.

2. The method of claim 1, wherein said heterologous nucleic acid encodes a selectable marker gene which confers resistance to a selection agent.

3. The method of claim 2, wherein expression of said selectable marker gene confers resistance to a selection agent selected from the group consisting of spectinomycin, kanamycin, hygromycin, streptomycin, phosphinotricin, basta, glyphosate, and bromxynil.

4. The method of claim 1, wherein said protein having excision activity is CRE, and said excision sites are LOX sites, and wherein two to four days after introduction of the said DNA construct, the cell of step c) is incubated in shoot regeneration medium and wherein said plant is regenerated in the absence of selection for T-DNA transfer.

5. The method of claim 1, wherein said recombinase and its cognate excision site are selected from the group listed in Table I.

6. The method of claim 1, wherein the construct of step b) is introduced into said cells via a method selected from the group consisting of Agroinfiltration, PEG fusion, biolistic delivery, $CaPO_4$-mediated transfection, and electroporation.

7. The method of claim 1, wherein said construct of step b) is introduced into said plant cell by agroinfiltration and is expressed in the nucleus of said plant cell.

8. The method of claim 1, wherein said plant cell is obtained from a plant selected from the group consisting of tobacco, rice, potato, oil seed rape, corn, and wheat.

9. The method of claim 1, wherein said protein having excision activity is phiC31 integrase and said excision sites are ATT sites.

* * * * *